(12) United States Patent
Lassen

(10) Patent No.: US 12,097,182 B2
(45) Date of Patent: *Sep. 24, 2024

(54) COMPOUNDS AND METHODS FOR TREATMENT OF INFLAMMATORY BOWEL DISEASE WITH EXTRA-INTESTINAL MANIFESTATIONS

(71) Applicant: Arena Pharmaceuticals, Inc., New York, NY (US)

(72) Inventor: Cheryl Geraldine Lassen, Zurich (CH)

(73) Assignee: Arena Pharmaceuticals, Inc., New York, NY (US)

( * ) Notice: Subject to any disclaimer, the term of this patent is extended or adjusted under 35 U.S.C. 154(b) by 58 days.

This patent is subject to a terminal disclaimer.

(21) Appl. No.: 17/968,232

(22) Filed: Oct. 18, 2022

(65) Prior Publication Data

US 2023/0092353 A1 Mar. 23, 2023

Related U.S. Application Data

(63) Continuation of application No. 16/486,436, filed as application No. PCT/US2018/000048 on Feb. 16, 2018, now Pat. No. 11,478,448.

(60) Provisional application No. 62/459,881, filed on Feb. 16, 2017, provisional application No. 62/459,870, filed on Feb. 16, 2017.

(51) Int. Cl.
| | |
|---|---|
| *A61K 31/404* | (2006.01) |
| *A61K 9/20* | (2006.01) |
| *A61K 45/06* | (2006.01) |
| *A61P 1/04* | (2006.01) |
| *A61P 17/02* | (2006.01) |

(52) U.S. Cl.
CPC .......... *A61K 31/404* (2013.01); *A61K 9/2018* (2013.01); *A61K 9/2054* (2013.01); *A61K 9/2059* (2013.01); *A61K 45/06* (2013.01); *A61P 1/04* (2018.01); *A61P 17/02* (2018.01)

(58) Field of Classification Search
CPC .. A61K 31/404; A61K 9/2018; A61K 9/2054; A61K 9/2059; A61P 1/00; A61P 1/04; A61P 17/00; A61P 17/02; A61P 37/00
See application file for complete search history.

(56) References Cited

U.S. PATENT DOCUMENTS

| | | | |
|---|---|---|---|
| 3,206,470 A | 9/1965 | William et al. | |
| 4,057,559 A | 11/1977 | Asselin et al. | |
| 4,476,248 A | 10/1984 | Gordon et al. | |
| 4,782,076 A | 11/1988 | Mobilio et al. | |
| 4,810,699 A | 3/1989 | Sabatucci et al. | |
| 5,221,678 A | 6/1993 | Atkinson et al. | |
| 5,776,967 A | 7/1998 | Kreft et al. | |
| 5,830,911 A | 11/1998 | Failli et al. | |
| 6,410,583 B1 | 6/2002 | Labelle et al. | |
| 6,960,692 B2 | 11/2005 | Kohno et al. | |
| 7,250,441 B2 | 7/2007 | Gopalsamy et al. | |
| 8,415,484 B2 | 4/2013 | Jones et al. | |
| 8,580,841 B2 | 11/2013 | Jones et al. | |
| 8,853,419 B2 | 10/2014 | Montalban et al. | |
| 9,126,932 B2 | 9/2015 | Jones et al. | |
| 9,175,320 B2 | 11/2015 | Montalban et al. | |
| 9,447,041 B2 | 9/2016 | Montalban et al. | |
| 9,522,133 B2 | 12/2016 | Jones et al. | |
| 10,301,262 B2 | 5/2019 | Blackburn et al. | |
| 10,676,435 B2 | 6/2020 | Blackburn | |
| 11,007,175 B2 | 5/2021 | Glicklich et al. | |
| 11,091,435 B2 | 8/2021 | Blackburn et al. | |
| 11,149,292 B2 | 10/2021 | Montalban et al. | |
| 11,478,448 B2 | 10/2022 | Lassen et al. | |
| 2003/0083269 A1 | 5/2003 | Brouillette et al. | |
| 2003/0211421 A1 | 11/2003 | Hanabata et al. | |
| 2004/0224941 A1 | 11/2004 | Seko et al. | |
| 2004/0254222 A1 | 12/2004 | Kohno et al. | |
| 2005/0004114 A1 | 1/2005 | Whitehouse et al. | |
| 2005/0009786 A1 | 1/2005 | Pan et al. | |
| 2005/0014724 A1 | 1/2005 | Marsilje et al. | |
| 2005/0014725 A1 | 1/2005 | Mi et al. | |
| 2005/0014728 A1 | 1/2005 | Pan et al. | |

(Continued)

FOREIGN PATENT DOCUMENTS

| | | |
|---|---|---|
| CN | 101980704 | 2/2011 |
| CN | 101981030 | 2/2011 |

(Continued)

OTHER PUBLICATIONS

"2.9.26 Specific Surface Area by Gas Adsorption," European Pharmacopoeia, 2008, 2811-2814.

Actelion, Clinical Trials.gov, "Multicenter, Randomized, Double-blind, Placebo-controlled, Phase IIa Study to Evaluate the Efficacy, Safety, and Tolerability of ACT-128800, an SIP1 Receptor Agonist, Administered for 6 Weeks to Subjects With Moderate to Severe Chronic Plaque Psoriasis" http://clinicaltrials.gov/ct2/show/NCT00852670, 2009.

Adams et al., "Etrasimod (APD334), an Oral, Next-Generation Sphingosine-1-Phosphate Receptor Modulator Inhibits the Development of Colitis in Lymphoid-Null Mice Injected with Colitogenic CD4+ T Cells," The FASEB Journal, Apr. 2017, 31(S1): 993.11-993.11.

(Continued)

*Primary Examiner* — Sarah Pihonak
(74) *Attorney, Agent, or Firm* — Zhigang Rao

(57) ABSTRACT

The present invention relates to, inter alia, methods of treatment and combinations of (R)-2-(7-(4-cyclopentyl-3-(trifluoromethyl)benzyloxy)-1,2,3,4-tetrahydrocyclopenta[b]indol-3-yl)acetic acid (Compound 1) useful for the treatment of extra-intestinal manifestations (EIM) in an individual with inflammatory bowel disease (BBD) and for the treatment of pyoderma gangrenosum (PG). In some embodiments, the methods further comprise administering Compound 1, or a pharmaceutically salt, solvate, or hydrate thereof, in combination with a therapeutically effective amount of a compound selected from the group consisting of: a corticosteroid, a 5-aminosalicylic acid derivative, and a TNF-alpha inhibitor; or a corticosteroid, an immunosuppressant, a biologic, an anti-inflammatory agent, and an antibiotic.

23 Claims, 4 Drawing Sheets

(56) References Cited

U.S. PATENT DOCUMENTS

| | | |
|---|---|---|
| 2005/0033055 A1 | 2/2005 | Bugianesi et al. |
| 2005/0239899 A1 | 10/2005 | Fecke et al. |
| 2006/0004010 A1 | 1/2006 | Habashita et al. |
| 2006/0063821 A1 | 3/2006 | Gopalsamy et al. |
| 2006/0079542 A1 | 4/2006 | Nestor |
| 2006/0122222 A1 | 6/2006 | Whitehouse et al. |
| 2006/0160771 A1 | 7/2006 | Kohno et al. |
| 2006/0211656 A1 | 9/2006 | Albert et al. |
| 2006/0223866 A1 | 10/2006 | Evindar et al. |
| 2007/0010494 A1 | 1/2007 | Ehrhardt et al. |
| 2007/0043014 A1 | 2/2007 | Doherty et al. |
| 2007/0060573 A1 | 3/2007 | Wortmann et al. |
| 2007/0149595 A1 | 6/2007 | Tanaka et al. |
| 2007/0149597 A1 | 6/2007 | Nishi et al. |
| 2007/0167425 A1 | 7/2007 | Nakade et al. |
| 2007/0173487 A1 | 7/2007 | Saha et al. |
| 2007/0173507 A1 | 7/2007 | Hirata |
| 2007/0191313 A1 | 8/2007 | Beard et al. |
| 2007/0191371 A1 | 8/2007 | Bennett et al. |
| 2007/0191468 A1 | 8/2007 | Nishi et al. |
| 2007/0244155 A1 | 10/2007 | Sharma et al. |
| 2007/0254886 A1 | 11/2007 | Habashita et al. |
| 2008/0051418 A1 | 2/2008 | Maekawa et al. |
| 2008/0153882 A1 | 6/2008 | Nishi et al. |
| 2008/0200535 A1 | 8/2008 | Ohmori et al. |
| 2008/0207584 A1 | 8/2008 | Habashita et al. |
| 2008/0319077 A1 | 12/2008 | Suzuki et al. |
| 2009/0004265 A1 | 1/2009 | Misselwitz et al. |
| 2009/0012093 A1 | 1/2009 | Fukatsu et al. |
| 2009/0076070 A1 | 3/2009 | Harada et al. |
| 2009/0131438 A1 | 5/2009 | Ono et al. |
| 2009/0137685 A1 | 5/2009 | Kojima et al. |
| 2009/0253802 A1 | 10/2009 | Kaneko |
| 2009/0325907 A1 | 12/2009 | Kohno et al. |
| 2010/0267778 A1 | 10/2010 | Kusuda et al. |
| 2010/0273806 A1 | 10/2010 | Jones et al. |
| 2010/0292233 A1 | 11/2010 | Jones et al. |
| 2011/0000153 A1 | 1/2011 | Albert |
| 2011/0039933 A1 | 2/2011 | Evindar et al. |
| 2011/0105471 A1 | 5/2011 | Burcham |
| 2011/0130409 A1 | 6/2011 | Jones |
| 2011/0159096 A1 | 6/2011 | Duran Lopez et al. |
| 2011/0160243 A1 | 6/2011 | Jones et al. |
| 2012/0064060 A1 | 3/2012 | Habashita et al. |
| 2012/0295947 A1 | 11/2012 | Montalban et al. |
| 2012/0329848 A1 | 12/2012 | Jones et al. |
| 2013/0184307 A1 | 7/2013 | Jones et al. |
| 2013/0203807 A1 | 8/2013 | Tarcic et al. |
| 2014/0038987 A1 | 2/2014 | Jones et al. |
| 2014/0155654 A1 | 6/2014 | Preda et al. |
| 2014/0350115 A1 | 11/2014 | Kostik et al. |
| 2014/0357690 A1 | 12/2014 | Montalban et al. |
| 2015/0336966 A1 | 8/2015 | Jones et al. |
| 2015/0284399 A1 | 10/2015 | Jones et al. |
| 2015/0335618 A1 | 11/2015 | Jones et al. |
| 2016/0016904 A1 | 1/2016 | Montalban et al. |
| 2016/0038506 A1 | 2/2016 | Podolski et al. |
| 2017/0159088 A1 | 6/2017 | Montalban et al. |
| 2017/0217885 A1 | 8/2017 | Jones et al. |
| 2018/0186738 A1 | 7/2018 | Blackburn et al. |
| 2018/0263958 A1 | 9/2018 | Glicklich et al. |
| 2019/0135752 A1 | 5/2019 | Jones et al. |
| 2019/0330153 A1 | 10/2019 | Blackburn et al. |
| 2020/0000770 A1 | 1/2020 | Lassen et al. |
| 2020/0016121 A1 | 1/2020 | Lassen et al. |
| 2020/0361869 A1 | 11/2020 | Blackburn et al. |
| 2020/0407316 A1 | 12/2020 | Jones et al. |
| 2021/0228545 A1 | 7/2021 | Christopher et al. |
| 2021/0386706 A1 | 12/2021 | Adams |
| 2022/0002244 A1 | 1/2022 | Blackburn et al. |
| 2022/0023258 A1 | 1/2022 | Naik |
| 2022/0142977 A1 | 5/2022 | Naik |

FOREIGN PATENT DOCUMENTS

| | | |
|---|---|---|
| CN | 102197038 | 9/2011 |
| CN | 105816453 | 8/2016 |
| CN | 106278999 | 1/2017 |
| EP | 0468785 | 1/1992 |
| EP | 1195165 | 4/2002 |
| EP | 1650186 | 4/2006 |
| EP | 1826197 | 8/2007 |
| EP | 2003132 | 12/2008 |
| EP | 1772145 | 3/2011 |
| EP | 2017263 | 11/2011 |
| GB | 1436893 | 5/1976 |
| JP | 2007-262009 | 10/2007 |
| WO | WO 91/06537 | 5/1991 |
| WO | WO 97/14674 | 4/1997 |
| WO | WO 00/64888 | 11/2000 |
| WO | WO 02/39987 | 5/2002 |
| WO | WO 02/064616 | 8/2002 |
| WO | WO 02/092068 | 11/2002 |
| WO | WO 03/029205 | 4/2003 |
| WO | WO 03/062252 | 7/2003 |
| WO | WO 03/073986 | 9/2003 |
| WO | WO 03/074008 | 9/2003 |
| WO | WO 03/061567 | 12/2003 |
| WO | WO 03/105771 | 12/2003 |
| WO | WO 2004/010949 | 2/2004 |
| WO | WO 2004/058149 | 7/2004 |
| WO | WO 2004/064806 | 8/2004 |
| WO | WO 2004/071442 | 8/2004 |
| WO | WO 2004/074297 | 9/2004 |
| WO | WO 2004/096752 | 11/2004 |
| WO | WO 2004/096757 | 11/2004 |
| WO | WO 2004/103279 | 12/2004 |
| WO | WO 2004/103306 | 12/2004 |
| WO | WO 2004/103309 | 12/2004 |
| WO | WO 2004/104205 | 12/2004 |
| WO | WO 2004/110979 | 12/2004 |
| WO | WO 2004/113330 | 12/2004 |
| WO | WO 2005/000833 | 1/2005 |
| WO | WO 2005/020882 | 3/2005 |
| WO | WO 2005/021503 | 3/2005 |
| WO | WO 2005/032465 | 4/2005 |
| WO | WO 2005/041899 | 5/2005 |
| WO | WO 2005/044780 | 5/2005 |
| WO | WO 2005/058295 | 6/2005 |
| WO | WO 2005/058848 | 6/2005 |
| WO | WO 2005/070886 | 8/2005 |
| WO | WO 2005/079788 | 9/2005 |
| WO | WO 2005/082089 | 9/2005 |
| WO | WO 2005/082841 | 9/2005 |
| WO | WO 2005/085179 | 9/2005 |
| WO | WO 2005/097745 | 10/2005 |
| WO | WO 2005/123677 | 12/2005 |
| WO | WO 2006/001463 | 1/2006 |
| WO | WO 2006/009092 | 1/2006 |
| WO | WO 2006/010379 | 2/2006 |
| WO | WO 2006/010544 | 2/2006 |
| WO | WO 2006/011554 | 2/2006 |
| WO | WO 2006/013948 | 2/2006 |
| WO | WO 2006/020951 | 2/2006 |
| WO | WO 2006/034337 | 3/2006 |
| WO | WO 2006/043149 | 4/2006 |
| WO | WO 2006/047195 | 5/2006 |
| WO | WO 2006/063033 | 6/2006 |
| WO | WO 2006/064757 | 6/2006 |
| WO | WO 2006/079406 | 8/2006 |
| WO | WO 2006/088944 | 8/2006 |
| WO | WO 2006/100631 | 9/2006 |
| WO | WO 2006/100633 | 9/2006 |
| WO | WO 2006/100635 | 9/2006 |
| WO | WO 2006/131336 | 12/2006 |
| WO | WO 2006/137019 | 12/2006 |
| WO | WO 2006/137509 | 12/2006 |
| WO | WO 2007/024922 | 3/2007 |
| WO | WO 2007/037196 | 4/2007 |
| WO | WO 2007/060626 | 5/2007 |
| WO | WO 2007/061458 | 5/2007 |
| WO | WO 2007/080542 | 7/2007 |

(56) References Cited

FOREIGN PATENT DOCUMENTS

| | | |
|---|---|---|
| WO | WO 2007/083089 | 7/2007 |
| WO | WO 2007/085451 | 8/2007 |
| WO | WO 2007/086001 | 8/2007 |
| WO | WO 2007/091396 | 8/2007 |
| WO | WO 2007/091501 | 8/2007 |
| WO | WO 2007/092190 | 8/2007 |
| WO | WO 2007/092638 | 8/2007 |
| WO | WO 2007/095561 | 8/2007 |
| WO | WO 2007/098474 | 8/2007 |
| WO | WO 2007/100617 | 9/2007 |
| WO | WO 2007/109330 | 9/2007 |
| WO | WO 2007/109334 | 9/2007 |
| WO | WO 2007/115820 | 10/2007 |
| WO | WO 2007/116866 | 10/2007 |
| WO | WO 2007/129473 | 11/2007 |
| WO | WO 2007/129745 | 11/2007 |
| WO | WO 2007/132307 | 11/2007 |
| WO | WO 2008/016674 | 2/2008 |
| WO | WO 2008/016692 | 2/2008 |
| WO | WO 2008/018427 | 2/2008 |
| WO | WO 2008/019090 | 2/2008 |
| WO | WO 2008/023783 | 2/2008 |
| WO | WO 2008/024196 | 2/2008 |
| WO | WO 2008/028937 | 3/2008 |
| WO | WO 2008/029306 | 3/2008 |
| WO | WO 2008/029371 | 3/2008 |
| WO | WO 2008/030843 | 3/2008 |
| WO | WO 2008/035239 | 3/2008 |
| WO | WO 2008/074820 | 6/2008 |
| WO | WO 2008/074821 | 6/2008 |
| WO | WO 2008/076356 | 6/2008 |
| WO | WO 2008/079382 | 7/2008 |
| WO | WO 2008/089015 | 7/2008 |
| WO | WO 2008/091967 | 7/2008 |
| WO | WO 2008/097819 | 8/2008 |
| WO | WO 2008/114157 | 9/2008 |
| WO | WO 2008/128951 | 10/2008 |
| WO | WO 2008/152149 | 12/2008 |
| WO | WO 2009/011850 | 1/2009 |
| WO | WO 2009/019167 | 2/2009 |
| WO | WO 2009/019506 | 2/2009 |
| WO | WO 2009/064250 | 5/2009 |
| WO | WO 2009/078983 | 6/2009 |
| WO | WO 2009/094157 | 7/2009 |
| WO | WO 2009/103552 | 8/2009 |
| WO | WO 2009/115954 | 9/2009 |
| WO | WO 2009/151529 | 12/2009 |
| WO | WO 2009/151621 | 12/2009 |
| WO | WO 2009/151626 | 12/2009 |
| WO | WO 2010/011316 | 1/2010 |
| WO | WO 2010/027431 | 3/2010 |
| WO | WO 2010/072703 | 7/2010 |
| WO | WO 2010/075239 | 7/2010 |
| WO | WO 2010/093704 | 8/2010 |
| WO | WO 2011/005290 | 1/2011 |
| WO | WO 2011/005295 | 1/2011 |
| WO | WO 2011/059784 | 5/2011 |
| WO | WO 2011/094008 | 8/2011 |
| WO | WO 2011/109471 | 9/2011 |
| WO | WO 2012/015758 | 2/2012 |
| WO | WO 2012/109108 | 8/2012 |
| WO | WO 2014/136282 | 9/2014 |
| WO | WO 2016/112075 | 7/2016 |
| WO | WO 2016/209809 | 12/2016 |
| WO | WO 2018/151834 | 8/2018 |
| WO | WO 2018/151873 | 8/2018 |

OTHER PUBLICATIONS

Allende et al., "Sphingosine-1-phosphate lyase deficiency produces a pro-inflammatory response while impairing neutrophil trafficking," J Biol Chem; 2011, 286:7348-58.

Ambooken et al., "Malignant pyoderma gangrenosum eroding the parotid gland successfully treated with dexamethasone pulse therapy," Int. J. Dermatol., 2014, 53:1536-1538.

American Gastroenterological Assoc. [online], "IBD emerges as a global disease," Jan. 5, 2012, retrieved on Jan. 7, 2015, retrieved from URL <www.sciencedaily.com/releases/2012/01/120104135402. htm>, 5 pages.

Arbiser, "Why targeted therapy hasn't worked in advanced cancer," J Clinical Invest., Oct. 2007, 117(10):2762-2765.

Arena Pharmaceuticals [online], "Arena Pharmaceuticals Reports Positive Phase 2 Results from the OASIS Trial for Etrasimod in Patients with Ulcerative Colitis," Mar. 19, 2018, retrieved Mar. 21, 2022, retrieved from URL <https://invest.arenapharm.com/news-releases/news-release-details/arena-pharmaceuticals-reports-positive-phase-2-results-oasis>, 5 pages.

Avoiding Fatal Responses to Flu Infection, ScienceDaily, http://www.sciencedaily.com/releases/2011/09/110915134410.htm, Sep. 15, 2011, 2 pages.

Balatoni et al., "FTY720 sustains and restores neuronal function in the DA rat model of MOG-induced experimental autoimmunue encephalomyelitis," Brain Res. Bull., 2007, 74:307-316.

Bar-Haim et al., "Interrelationship between Dendritic Cell Trafficking and Francisella tularensis Dissemination following Airway Infection," PLoS Pathog., 2008, 4(11):e1000211, 15 pages.

Baumruker et al., "FTY720, an immunomodulatory sphingolipid mimetic: translation of a novel mechanism into clinical benefit in multiple sclerosis," Expert Opin. Investig. Drugs, 2007, 16(3):283-289.

Bergasa et al., "Pruritus and fatigue in primary biliary cirrhosis," Best Practice & Research Clinical Gastroenterology, Aug. 2000, 14(4):643-655.

Berge et al., "Pharmaceutical Salts," J Pharma Sci., 1977, 66(1):1-19.

Biopharmatiques, "Merging Pharma and Biotech", http://www.biopharmaceutiques.com/fr/tables/clinical_studies_709.html, 2009, 1 page.

Boismenu et al., "Insights from mouse models of colitis," K. Leukoc Biol, 67:267-278, 2000.

Bolick et al., "Sphingosine-1-Phosphate Prevents Tumor Necrosis Factor-alpha-Mediated Monocyte Adhesion to Aortic Endothelium in Mice," Arterioscler. Thromb. Vasc. Biol., 2005, 25:976-981.

Brinkmann et al., "Fingolimod (FTY720): discovery and development of an oral drug to treat multiple sclerosis," Nat Rev Drug Discov, Nov. 2010; 9(11):883-97.

Brinkmann et al., "FTY720 Alters Lymphocyte Homing and Protects Allografts Without Inducing General Immunosuppression," Transplantation Proc., 2001, 33:530-531.

Brinkmann et al., "FTY720: Altered Lymphocyte Traffic Results in Allograft Protection," Transplantation, Sep. 2001, 72(5):764-769.

Brinkmann et al., "The Immune Modulator FTY720 Targets Sphingosine 1-Phosphate Receptors," J Biol. Chem., 2002, 277(24):21453-21457.

Brinkmann, "Sphingosine 1-phosphate receptors in health and disease: Mechanistic insights from gene deletion studies and reverse pharmacology," Pharmacol. Ther., 2007, 115:84-105.

Brinkmann, "FTY720 (fingolimod) in Multiple Sclerosis: therapeutic effects in the immune and the central nervous system", British Journal of Pharmacology, 158: 1173-1182, 2009.

Brossard et al., "Pharmacokinetics and pharmacodynamics of ponesimod, a selective S1P1 receptor modulator, in the first-in-human study," British Journal of Clinical Pharmacology, Dec. 2013, 76(6):888-896.

Brunauer et al., "Adsorption of Gases in Multimolecular Layers," J. Am. Chem. Soc., Feb. 1938, 60(2):309-319.

Brunsting et al. "Pyoderma (Echthyma) Gangrenosum Clinical and Experimental Observations in Five Cases Occurring in Adults," Arch Dermatol Syph, 1930, 22:655-680.

Budde et al., "First Human Trial of FTY720, a Novel Immunomodulator, in Stable Renal Transplant Patients," J Am Soc. Nephrol., 2002, 13:1073-1083.

Burisch et al., "The burden of inflammatory bowel disease in Europe," J Crohns Colitis., 2013, 7(4):322-37.

(56) References Cited

OTHER PUBLICATIONS

Buzard, Daniel J et al., "Recent Progress in the Development of Selective S1P1 Receptor Agonists for the Treatment of Inflammatory and Autoimmune Disorders", Expert Opinion, 1141-1159, 2008.

Buzard et al., "Discovery of APD334: design of a clinical stage functional antagonist of the sphinogosine-1-phosphate-1 receptor," ACS Med. Chem. Lett., 2014, 5(12):1313-1317.

Buzard et al., "Discovery and Characterization of Potent and Selective 4-Oxo-4-(5-(5-phenyl-1,2,4-oxadiazol-3-yl)indolin-1-yl)butanoic acids as S1P1 Agonists", Biorganic Med. Chem. Lett., 2011, 6013-6018.

Buzard, Daniel J. et al., "Discovery and Characterization of Potent and Selective 4-Oxo-4-(5-(5-phenyl-1,2,4-oxadiazol-3-yl)indolin-1-yl)butanoic acids as S1P1 Receptor Agonists", Arena Pharmaceuticals, Inc., MEDI099, ACS, Mar. 2011, 1 page.

Centers for Disease Control and Prevention [online], "Inflammatory bowel disease (IBD)," last reviewed Mar. 14, 2017, retrieved on Aug. 20, 2019, retrieved from URL <https://www.cdc.gov/ibd/>, 2 pages.

Chawla et al., Challenges in Polymorphism of Pharmaceuticals, CRIPS, Jan.-Mar. 2004, vol. 5, No. 1, 4 pages.

Cheung et al., "Combined ursodeoxycholic acid (UDCA) and fenofibrate in primary biliary cholangitis patients with incomplete UDCA response may improve outcomes," Aliment Pharmacol Ther., Nov. 2015, 43(2):283-293.

Chiba et al., "Role of Sphingosine 1-Phosphate Receptor Type 1 in Lumphocyte Egress from Secondary Lymphoid Tissues and Thymus," Cell Mole Immunol., Feb. 2006, 3(1):11-19.

Chiba, "FTY720, a new class of immunomodulator, inhibits lymphocyte egress from secondary lymphoid tissues and thymus by agonistic activity at sphingosine 1-phosphate receptors," Pharmacol. Ther., 2005, 108:308-319.

Chun et al., "International Union of Pharmacology. XXXIV. Lysophospholipid Receptor Nomenclature," Pharmacol. Rev., 2002, 54(2):256-269.

Clinical Trials [online], "Efficacy and Safety of Etrasimod (APD334) in Inflammatory Bowel Disease Patients With Active Skin Extraintestinal Manifestations," Dec. 31, 2020, Retrieved Jan. 25, 2022, retrieved from URL <https://clinicaltrials.gov/ct2/show/NCT03139032?term-etrasimod&draw-3&rank=13>, 32 pages.

Coelho et al., "The Immunomodulator FTY720 has a direct cytoprotective effect in oligodendrocyte Progenitors," J Pharmacol. Exp. Ther., 2007, 323:626-635.

Cohen, "Neutrophilic dermatoses: a review of current treatment options," Am J Clin Dermatol., 2009, 10(5):301-12.

Collier et al, "Radiosynthesis and In-vivo Evaluation of the Psuedopeptide 8-pioid Antagonist [$^{125}$I]-ITIPP(Ψ)," J. Labelled Compd. Radiopharm., 1999, 42, S264-S266.

Combes et al., "Methotrexate (MTX) plus ursodeoxycholic acid (UDCA) in the treatment of primary biliary cirrhosis," Hepatology, 2005, 42(5):1184-1193.

Coste et al., "Antinociceptive activity of the S1P-receptor agonist FTY720," J Cell Moll Med., 2008, 12(3):995-1004.

Crohn's and Colitis Foundation of America. The Facts About Inflammatory Bowel Diseases. Nov. 2014, New York, NY 10017. http://www.ccfa.org/assets/pdfs/ibdfactbook.pdf. Accessed Jan. 7, 2015.

Crosby et al., "030 Etrasimod, an oral, selective sphingosine 1-phosphate receptor modulator improves skin inflammation in a contact hypersensitivity dermatitis model," Journal of Investigative Dermatology, 2019, 139(9):Supplement 219, 1 page.

D'Ambrosio et al., "Ponesimod, a selective S1P1 receptor modulator: a potential treatment for multiple sclerosis and other immune-mediated diseases," Therapeutic Advances in Chronic Disease, 2016, 7(1):18-33.

Danese et al., "Ulcerative colitis," N Engl J Med, 2011, 365(18):1713-1725.

Daniel et al., "FTY720 Ameliorates Th1-Mediated Colitis in Mice by Directly Affecting the Functional Activity of DC4+CD25+ Regulatory T Cell1," J Immunol., 2007, 178:2458-2468.

Deguchi et al., "The S1P receptor modulator FTY720 prevents the development of experimental colitis in mice," Oncol. Rep., 2006, 16:699-703.

Dev et al., "Brain sphingosine-1-phosphate receptors: Implication for FTY720 in the treatment of multiple sclerosis," Pharmacol Ther., 2008, 117:77-93.

Dillmann et al., "S1PR4 Signaling Attenuates ILT 7 Internalization To Limit IFN-α Production by Human Plasmacytoid Dendritic Cells," J Immunol., 2016, 15;196(4):1579-90.

Feng et al., "Research Progress on Extraintestinal Manifestations of Inflammatory Bowel Disease," Journal of Gastroenterology and Hepatology, 2015, 24(6):631-640 (with English abstract).

Fenofibrate Prescribing Information, Revised Nov. 2018, 19 pages.

Fischer et al., "What rheumatologists can learn from gastroenterologists," Zeitschrift für Rheumatologie, 2018, 77(6):460-468, 10 pages (with English abstract).

Fischer et al., "Targeting receptor tyrosine kinase signalling in small cell lung cancer (SCLC): What have we learned so far?" Cancer Treatment Revs., 2007, 33:391-406.

Freling et al., "Cumulative incidence of, risk factors for, and outcome of dermatological complications of anti-TNF therapy in inflammatory bowel disease: a 14-year experience," Am J Gastroenterol, 2015, 110:1186-1196.

Fu et al., "Long-term islet graft survival in streptozotocin- and autoimmune-induced diabetes models by immunosuppressive and potential insulinotropic agent FTY720," Transplantation, May 2002, 73(9):1425-1430.

Fujii et al., "FTY720 suppresses CD4+CD44highCD62L-effector memory T cell-mediated colitis," Am J Physiol Gastrointest Liver Physiol., 2006, 291:G267-G274.

Fujino et al., "Amelioration of experimental autoimmune encephalomyelitis in Lewis rats by FTY720 treatment," J Pharmacol. Exp. Ther., 2003, 305(1):70-77.

Fujishiro et al., "Change from Cyclosporine to Combination Therapy of Mycophenolic Acid with the New Sphinogosine-1-phosphate Receptor Agonist, KRP-203, Prevents Host Nephrotoxicity and Transplant Vasculopathy in Rats," J Heart Lung Transplant, 2006, 25:825-833.

Gabriel et al., "High throughput screening technologies for direct cyclic AMP measurement", ASSAY and Drug Development Technologies, 2003, 1(2):291-303.

Gameiro et al., "Pyoderma gangrenosum: challenges and solutions" Clin. Cos. Inv. Dermatol, 2015, 8:285-293.

GeneMedRX [online], "Cytochrome P-450 (CYP) Metabolism Reference Table," available on or before Nov. 8, 2017, via Internet Archive: <https://web.archive.org/web/20171108224330/http://www.genemedrx.com/Cytochrome_P450_Metabolism_Table.php>, retrieved on Mar. 23, 2022, URL <http://www.genemedrx.com/Cytochrome_P450_Metabolism_Table.php>, 3 pages.

Gergely et al., "The selective sphingosine 1-phosphate receptor modulator BAF312 redirects lymphocyte distribution and has species-specific effects on heart rate," British J of Pharm, 2012, 167(5):1035-1047.

Golub et al., "Molecular Classification of Cancer: Class Discovery and Class Prediction by Gene Expression Monitoring," Science, 1999, 286:531-537.

Gottlieb, et al., "NMR Chemical Shifts of Common Laboratory Solvents as trace Impurities," *J. Org. Chem*. 1997, 62, 7512-7515.

Griesser, "The Importance of Solvates" in *Polymorphism in the Pharmaceutical Industry*, 211-233 (Rolf Hilfiker, ed., 2006).

Groeneveld, "Vascular pharmacology of acute lung injury and acute respiratory distress syndrome," Vascular Pharmacol., 2003, 39:247-256.

Guerrero et al., "Sphingosine 1-phosphate receptor 1 agonists: a patent review (2013-2015)," Expert Opinion on Therapeutic Patents, 2016, 26(4):455-470, 41 pages.

Guillory, "Generation of Polymorphs, Hydrates, Solvates, and Amorphous Solids," in: Polymorphism in Pharmaceutical Solids, ed. Harry G.Brittan, vol. 95, Marcel Dekker, Inc. New York, 1999, pp. 202-209.

(56) References Cited

OTHER PUBLICATIONS

Hale et al., "Potent S1P receptor agonists replicate the pharmacologic actions of the novel immune modulator FTY720," Bioorganic Med Chem. Lett., 2004, 14:3351-3355.

Han, Sangdon et al., "Discovery of 2-(7-(5-phenyl-1,2,4-oxadiazol-3-yl)-1,2,3,4-tetrahydrocyclopenta[b]indol-3-yl)acetic acids: Potent and Selective Sphingosine-1-phosphate (S1P1) Receptor Agonists", Arena Pharmaceuticals, Inc., MEDI 098, ACS Poster, Mar. 2011,1 page.

Herzinger et al., "Sphingosine-1-Phosphate Signaling and the Skin," Am J Clin Dermatol., 2007, 8(6):329-336.

Hinchcliff et al., "Systemic Sclerosis/Scleroderma: A Treatable Multisystem Disease," Am Fam Physician, Oct. 2008, 78(8):961-968.

Hwang et al., "FTY720, a New Immunosuppressant, Promotes Long-Term Graft Survival and Inhibits the Progression of Graft Coronary Artery Disease in a Murine Model of Cardiac Transplantation," Circulation, 1999, 100:1322-1329.

Idzko et al., "Local application of FTY720 to the lung abrogates experimental asthma by altering dendritic cell function," J Clinc Invest., Nov. 2006, 116(11):2935-2944.

International Search Report and Written Opinion in Application No. PCT/US2018/000091, dated May 6, 2018, 8 pages.

International Search Report and Written Opinion in Appln. No. PCT/US2018/000048, dated Aug. 23, 2018.

International Standard, "Determination of the specific surface area of solids by gas adsorption—BET method," 2010, Second Edition, 1-24.

Ishii et al., "Sphingosine-1-phosphate mobilizes osteoclast precursors and regulates bone homeostasis," Nature, Mar. 2009, 458(7237):524-528.

Jones, "The Discovery of APD334, A Selective S1P1 Functional Antagonist", EFMC-ISMC (2014), Sep. 8, 2014 (PowerPoint), 22 pages.

Jones, Robert M., "Discovery of Potent and Selective Sphingosine-1-Phosphate 1 (S1P1) Receptor Agonists", CHI 6$^{th}$ Annual Drug Discovery Chemistry, San Diego, CA, Apr. 12, 2011, 22 pages.

Jones, Robert M., "Discovery of Potent and Selective Sphingosine-1-Phosphate 1(S1P1) Receptor Agonists", CHI 6$^{th}$ Annual Discovery on Target, Boston, MA, Nov. 3, 2011, 26 pages.

Jung et al., "Functional Consequences of S1P Receptor Modulation in Rat Oligodendroglial Lineage Cells," Glia, 2007, 55:1656-1667.

Kaneider et al., "The immune modulator FTY720 targets sphingosine-kinase-dependent migration of human monocytes in response to amyloid beta-protein and its precursor," FASEB J, 2004, 18:309-311.

Kappos et al., "A placebo-controlled trial of oral fingolimod in relapsing multiple sclerosis," N Engl J Med., 2010, 362(5):387-401.

Kappos et al., "Oral Fingolimod (FTY720) for Relapsing Multiple Sclerosis," N Engl J Med., 2006, 355:1124-1140.

Karimian et al., "Sphingosine kinase-1 inhibition protects primary rat hepatocytes against bile salt-induced apoptosis," Biochim Biophys Acta., 2013, 1832(12):1922-9.

Kataoka et al., "FTY720, Sphingosine 1-Phosphate Receptor Modulator, Ameliorates Experimental Autoimmune Encephalomyelitis by Inhibition of T Cell Infiltration," Cell Mol. Immunol., Dec. 2005, 2(6):439-448.

Kaudel et al., "FTY720 for Treatment of Ischemia-Reperfusion Injury Following Complete Renal Ischemia; Impact on Long-Term Survival and T-Lymphocyte Tissue Infiltration," Transplantation Proc., 2007, 39:499-502.

Kawasaki, Andrew et al., "Discovery and Characterization of 2-(7-(5-phenyl-1,2,4-oxadiazol-3-yl)-2,3-dihydro-1H-pyrrolo[1,2-a]indol-1-yl)acetic acid Derivatives as Potent & Selective Human S1P1 Receptor Agonists", Arena Pharmaceuticals, Inc., MEDI254, ACS, Mar. 2011, 1 page.

Keul et al., "The Sphinogosine-1-Phosphate Analogue FTY720 Reduces Atherosclerosis in Apolipoprotein E-Deficient Mice," Arterioscler Thromb Vasc Biol., 2007, 27:607-613.

Kim et al., "Sphingosine-1-phosphate inhibits human keratinocyte proliferation via Akt/protein kinase B inactivation," Cell Signal, 2004, 16:89-95.

Kimura et al., "Essential Roles of Sphingosine 1-Phosphate/S1P1 Receptor Axis in the Migration of Neural Stem Cells Toward a Site of Spinal Cord Injury," Stem Cells, 2007, 25:115-124.

Kitabayashi et al., "FTY720 Prevents Development of Experimental Autoimmune Myocarditis Through Reduction of Circulating Lymphocytes," J Cardiovasc. Pharmacol. 2000, 35:410-416.

Kohno et al., "A Novel Immunomodulator, FTY720, Prevents Development of Experimental Autoimmune Myasthenia Gravis in C57BL/6 Mice," Biol Pharma Bull., 2005, 28(4):736-739.

Kohno et al., "A Novel Immunomodulator, FTY720, Prevents Spontaneous Dermatitis in NC/Nga Mice," Biol. Pharm. Bull., 2004, 27(9):1392-1396.

Komori et al., "Effect of Etrasimod on Circulating Lymphocyte Subsets: Data from a Randomized Phase 1 Study in Healthy Japanese and Caucasian Men", The American Journal of Gastroenterology, Dec. 2020, 115: p. S12.

Koreck et al., "The role of innate immunity in the pathogenesis of acne," Dermatol., 2003, 206:96-105.

Kovarick et al., "Multiple-Dose FTY720: Tolerability, Pharmacokinetics, and Lymphocyte Responses in Healthy Subjects," The Journal of Clinical Pharmacology, May 2004, 44(5):532-537.

Kurose et al., "Effects of FTY720, a novel immunosuppressant, on experimental autoimmune uveoretinitis in rats," Exp. Eye Res., 2000, 70:7-15.

Lala et al., "Role of nitric oxide in tumor progression: Lessons from experimental tumors," Cancer Metastasis Rev., 1998, 17:91-106.

LaMontagne et al., "Antagonism of Sphingosine-1-Phosphate Receptors by FTY720 Inhibits Angiogenesis and Tumor Vascularization," Cancer Res., 2006, 66:221-231.

Le Bas, et al., "Radioiodinated Analogs of EP 00652218 for the Exploration of the Tachykinin NK1 Receptor by Spect," J. Labelled Compl. Radiopharm. 2001, 44, S280-S282.

Lee et al., "FTY720: A Promising Agent for Treatment of Metastatic Hepatocellular Carcinoma," Clin. Cancer Res., 2005, 11:8458-8466.

Lima et al., "FTY720 Treatment Prolongs Skin Graft Survival in a Completely Incompatible Strain Combination," Transplant Proc., 2004, 36:1015-1017.

Liu et al., "Long-Term Effect of FTY720 on Lymphocyte Count and Islet Allograft Survival in Mice," Microsurgery, 2007, 27:300-304.

Lleo et al., "Etiopathogenesis of primary viliary cirrhosis," *World J Gastroenterol*, Jun. 2008, 14(21):3328-3337.

Loftus, "Clinical epidemiology of inflammatory bowel disease: Incidence, prevalence, and environmental influences," Gastroenterology, 2004; 126(6):1504-17.

Luo et al., "Clinical manifestations and therapy of extraintestinal manifestations with inflammatory bowel disease," International Journal of Digestive Diseases, 2006, pp. 87-90 (with English abstract).

Madhusudan et al., "Tyrosine kinase inhibitors in cancer therapy," Clinical Biochem., 2004, 37:618-635.

Maki et al., "Prevention and Cure of Autoimmune Diabetes in Nonobese Diabetic Mice by Continuous Administration of FTY720," Transplantation, 2005, 79:1051-1055.

Maki et al., "Prevention of autoimmune diabetes by FTY720 in Nonobese diabetic mice," Transplantation, Dec. 2002, 74(12):1684-1686.

Martini et al., "Current perspectives on FTY720," Expert Opin. Investig. Drugs, 2007, 16:505-518.

Martini et al., "S1P modulator FTY720 limits matrix expansion in acute anti-thy1 mesangioproliferative glomerulonephritis," Am J Physiol Renal Physiol., 2007, 292:F1761-F1770.

Marzano et al., "Cutaneous manifestations in patients with inflammatory bowel diseases: pathophysiology, clinical features, and therapy," Inflamm. Bowel Dis., 2014, 20:213-227.

Marzano et al., "Role of inflammatory cells, cytokines and matrix metalloproteinases in neutrophil-mediated skin diseases," Experimental Immunology, 2010, 162:1-11.

(56) References Cited

OTHER PUBLICATIONS

Matloubian et al., "Lymphocyte egress from thymus and peripheral lymphoid organs in dependent on SIP receptor 1," Nature, Jan. 2004, 427:355-360.
Matsuura et al., "Effect of FTY720, a novel immunosuppressant, on adjuvant- and collagen-induced arthritis in rats," Int. J Immunopharmacol. 2000, 22:323-331.
Matsuura et al., "Effect of FTY720, a novel immunosuppressant, on adjuvant-induced arthritis in rats," Inflamm. Res. 2000, 49:404-410.
Medscape [online], "Inflammatory Bowel Disease: Practice Essentials," Accessed Jan. 8, 2015, Last Updated Apr. 10, 2020, retrieved from URL <https://emedicine.medscape.com/article/179037-overview>, 2 pages.
Miron et al., "FTY720 Modulates Human Oligodendrocyte Progenitor Process Extension and Survival," Ann Neurol, 2008, 63:61-71.
Miyamoto et al., "Therapeutic Effects of FTY720, a New Immunosuppressive Agent, in a Murine Model of Acute Viral Myocarditis," J Am Coll Cardiol., 2001, 37(6):1713-1718.
Mizushima et al., "Therapeutic Effects of a New Lymphocyte Homing Reagent FTY720 in Interleukin-10 Gene-deficient Mice with Colitis," Inflamm Bowel Dis., May 2004, 10(3):182-192.
Morissette, et al., "High-Throughput Crystallization: Polymorphs, Salts, Co-Crystals and Solvates", Adv. Drug Delivery Rev., 56:275-300 (2004).
Nakashima et al., "Impaired Initiation of Contact Hypersensitivity by FTY720," J Invest Dermatol., 2008, 128:2833-2841.
Nestle et al., "Plasmacytoid predendritic cells initiate psoriasis through interferon-alpha production," J Exp Med., 2005, 202(1):135-43.
Neurath et al., "Antibodies to Interleukin 12 Abrogate Established Experimental Colitis in Mice," J. Exp. Med, 182:1281-1290, 1995.
Newman et al., "Solid-state analysis of active pharmaceutical ingredient in drug products," DDT, Oct. 2003, 8(19):898-905.
Nofer et al., "FTY720, a Synthetic Sphingosine 1 Phosphate Analogue, Inhibits Development of Atherosclerosis in Low-Density Lipoprotein Receptor Deficient Mice," Circulation, 2007, 115:501-508.
Ogawa et al., "A novel sphingosine-1-phosphate receptor agonist KRP-203 attenuates rate autoimmune myocarditis," Biochem. Biophys. Res. Commun., 2007, 361:621-628.
Okayasu et al., "A Novel Method in the Induction of Reliable Experimental Acute and Chronic Ulcerative Colitis in Mice," Gastroenterology, 98:694-702, 1990.
Okazaki et al., "Effects of FTY720 in MRL-lpr/lpr mice: therapeutic potential in systemic lupus erythematosus," J Rheumatol., 2002, 29:707-716.
Oo et al., "Immunosuppressive and Anti-angiogenic Sphingosine 1-Phosphate Receptor-1 Agonists Induce Ubiquitinylation and Proteasomal Degradation of the Receptor," J Biol Chem., 2007, 282(12):9082-9089.
Pan et al., "A Monoselective Sphingosine-1-Phosphate Receptor-1 Agonist Prevents Allograft Rejection in a Stringent Rat Heart Transplantation Model," Chem. Biol., 2006, 13:1227-1234.
Paul et al., "Evidence-based recommendations on topical treatment and phototherapy of psoriasis: systematic review and expert opinion of a panel of dermatologists," J Eur Acad Dermatol Venereol, 2012, 26 (suppl 3): 1-10.
Pfeilschifter et al., "Treatment with the immunomodulator FTY720 does not promote spontaneous bacterial infections after experimental stroke in mice," Experimental Translational Stroke Med., 2011, 36 pages.
Premenko-Lanier et al., "Transient FTY720 treatment promotes immune-mediated clearance of a chronic viral infection," Nature, Aug. 2008, 454:894-899.
prnewswire.com [online], "Arena Pharmaceuticals Reports Positive Long-Term Data from the Open-Label Extension of the Phase 2 OASIS Trial Evaluating Etrasimod for Treatment of Ulcerative Colitis," Jan. 2019, retrieved on Mar. 25, 2022, retrieved from URL <https://www.prnewswire.com/news-releases/arena-pharmaceuticals-reports-positive-long-term-data-from-the-open-label-extension-of-the-phase-2-oasis-trial-evaluating-etrasimod-for-treatment-of-ulcerative-colitis-300773493.html>, 2 pages.
Quaglino et al., "Phenotypical characterization of circulating cell subsets in pyoderma gangrenosum patients: the experience of the Italian immuno-pathology group," J Eur Acad Dermatol Venereal, 2016, 30(4):655-8.
Rasenack et al., "Crystal habit and tableting behavior," International Journal of Pharmaceutics, Sep. 2002, 244(1-2): 45-57.
Rausch et al., "Predictability of FTY720 efficacy in experimental autoimmune encephalomyelitis by in vivo macrophage tracking: Clinical implications for ultrasmall superparamagnetic iron oxide-enhanced magnetic resonance imaging," J Magn. Reson. Imaging, 2004, 20:16-24.
Raveney et al., "Fingolimod (FTY720) as an Acute Rescue Therapy for Intraocular Inflammatory Disease," Arch Ophthalmol, 2008, 126(10):1390-1395.
Reines et al., "Topical application of sphingosine-1-phosphate and FTY720 attenuate allergic contact dermatitis reaction through inhibition of dendritic cell migration," J Clin Invest Dermatol, 2009, 129(8):1954-62.
Reinisch et al., "Adalimumab for induction of clinical remission in moderately to severely active ulcerative colitis: results of a randomised controlled trial," Gut, 2011, 60:780-787.
Reshetnyak, "Primary biliary cirrhosis: Clinical and laboratory criteria for its diagnosis," World J of Gastroenterology, 2015, 21(25):7683-7708.
Rheumatoid Arthritis Health Center—Most Common Types of Arthritis, WebMD, http://www.webmd.com/rheumatoid-arthritis/guide/most-common-arthritis-types, 2012, 2 pages.
RN 380350-42-5, STN/CAPLUS, 2002, 1 page.
Ronald Hoffman, M.D., "Crohns disease and ulcerative colitis," Sep. 1995, http://www.drhoffman.com/page.cfm/171, 5 pages.
Rosen et al., "Egress: a receptor-regulated step in lymphocyte trafficking," Immunol. Rev. 2003, 195:160-177.
Rudic et al., "Ursodeoxycholic acid for primary biliary cirrhosis," Cochrane Database of Systematic Reviews, Dec. 2012, 1-139.
Ruocco et al., "Pyoderma gangrenosum: an updated review," Eur. Acad. Dermatol & Venereology, 2009, 23:1008-1017.
Sakagawa et al., "Rejection following donor or recipient preoperative treatment with FTY720 in rat small bowel transplantation," Transpl. Immunol., 2004, 13:161-168.
Sanchez et al., "Phosphorylation and Action of the Immunomodulator FTY720 Inhibits Vascular Endothelial Cell Growth Factor-induced Vascular Permeability," J Biol Chem., 2003, 278(47):47281-47290.
Sandborn et al., "Efficacy and Safety of Etrasimod in a Phase 2 Randomized Trial of Patients with Ulcerative Colitis," Gastroenterology, Feb. 2020, 158(3):550-561.
Sandborn et al., "UEG Week 2018 Oral Presentations OP242—'A Randomized Double-Blind Placebo-Controlled Trial of A Selective, Oral Sphingosine 1-Phosphate Receptor Modulator, Etrasimod (ADP334), In Moderate To Severe Ulverative Colitis: Results From The Oasis Study'" United European Gastroenterology Journal, 2018, 6:A94-A95.
Sanna et al., "Enhancement of capillary leakage and restoration of lymphocyte egress by a chiral SIP1 antagonist in vivo," Nature Chem Biol., Aug. 2006, 2(8):434-441.
Sanna et al., "Sphingosine 1-Phosphate (SIP) Receptor Subtypes SIP1 and SIP3, Respectively, Regulate Lymphocyte Recirculation and Heart Rate," J. Biol Chem., 2004, 279(14):13839-13848.
Sauer et al., "Involvement of Smad Signlaing in Sphingosine 1-Phosphate-mediated Biological Responses of Keratinocytes," J Biol. Chem., 2004, 279:38471-38479.
Sawicka et al., "Inhibition of Th1- and Th2-Mediated Airway Inflammation by the Sphingosine 1-Phosphate Receptor Agonist FTY720," J Immunol., 2003, 171:6206-6214.
Schaper et al., "Sphingosine-1-phosphate differently regulates the cytokine production of IL-12, IL-23 and IL-27 in activated murine bone marrow derived dendritic cells," Mol Immunol., 2014, 59(1):10-8.

(56) References Cited

OTHER PUBLICATIONS

Schmid et al., "The Immunosuppressant FTY720 inhibits tumor Angiogenesis via the Sphingosine 1-Phosphate Receptor 1," J Cell Biochem., 2007, 101:259-270.
Schuppel et al., "Sphingosine 1-phosphate restrains insulin-mediated keratinocyte proliferation via inhibition of Akt through the SIP2 receptor subtype," J Invest Dermatol, 2008, 128:1747-56.
Schwab and Cyster, "Finding a way out: lymphocyte egress from lymphoid organs," Nature Immunol., Dec. 2007, 8(12):1295-1301.
Shafiee et al., "An efficient enzyme-catalyzed kinetic resolution: large-scale preparation of an enantiomerically pure indole-ethyl ester derivative, a key component for the synthesis of a prostaglandin D2 receptor antagonist, an anti-allergic rhinitis drug candidate," Tetrahedron: Asymmetry, Sep. 2005, 16:3094-3098.
Shimizu et al., "KRP-203, a Novel Synthetic Immunosuppressant, Prolongs Graft Survival and Attenuates Chronic Rejection in Rat Skin and Heart Allografts," Circulation, 2005, 111:222-229.
Shtukenberg et al., "Spherulites," Chemical Reviews, 2012, 112: 1805-1838.
Smith et al., "Clinical, molecular, and genetic characteristics of PAPA syndrome: a review," Current Genomics, 2010, Bentham Science Publ., 11:519-527.
Stahly, "Diversity in Single- and Multiple-Component Crystals. The Search for and Prevalence of Polymorphs and Cocrystals," Crystal Growth & Design (2007), 7(6), 1007-1026.
STN Search Report dated May 22, 2017, 1 pages (RN 380350-42-5, STN/CAPLUS (Year: 2002).
Storey, et al., "Automation of Solid Form Screening Procedures in the Pharmaceutical Industry—How to Avoid the Bottlenecks", Crystallography Reviews, 10(1):45-46 (2004).
Sturino et al: "Discovery of a potent and selective prostaglandin D2 receptor antagonist, [(3R)-4-(4-chloro-benzyl)-7-Fluoro-5-(methylsulfonyl)-1,2,3,4-tetrahydrocyclopenta[b]indol-3-yl]-acetic acid (MK-0524)", Journal of Medicinal Chemistry, Feb. 22, 2007, pp. 794-806.
Su et al., "Histopathologic and immunopathologic study of pyoderma gangrenosum," J Cut. Path, 1986, 13(5):323-330.
Suzuki et al., "Efficacy of Mycophenolic Acid Combined with KRP-203, a Novel Immunomodulator, in a Rat Heart Transplantation Model," J Heart Lung Transplant, 2006, 25:302-309.
Suzuki et al., "Immunosuppressive effect of a new drug, FTY720, on lymphocyte responses in vitro and cardiac allograft survival in rats," Transplant Immunol., 1996, 4:252-255.
Tavarela, "Review article: Skin complications associated with inflammatory bowel disease," Aliment Pharmacol Ther, 2004, Suppl 4:50-53.
Taylor et al., "Insights into the mechanism of FTY720 and compatibility with regulatory T cells for the inhibition of graft-versus-host disease (GVHD)," Blood, 2007, 110:3480-3488.
The Pocket Oxford American Dictionary of Current English, "Advise" and "Prescribe" Oxford University Press, New York: 2002, pp. 11 and 623.
Truong et al., "Human Islet Function is not Impaired by the Sphingosine-1-Phosphate Receptor Modulator FTY720," Am J Transplantation, 2007, 7:2031-2038.
Truppo et al., "Optimization and Scale-Up of a Lipase-Catalyzed Enzymatic Resolution of an Indole Ester Intermediate for a Prostaglandin D2 (DP) Receptor Antagonist Targeting Allergic Rhinitis," Organic Process Research and Development, Feb. 2006, 10(3):592-598.
U.S. Department of Health & Human Services National Institutes of Health [online], "Pyoderma gangrenosum," Last updated Aug. 15, 2016, retrieved on Aug. 20, 2019, 7 pages.
United States Pharmacopeial Convention, USP35 NF30, 2012: U. S. Pharmacopoeia National Formulary, Optical Microscopy, Physical Tests, 2012, 331-334.
Vachal et al., "Highly selective and potent agonists of sphinogosin-1-phosphate 1 (S1P1) receptor," Bioorganic Med Chem Lett., Jul. 2006, 16(14):3684-3687.

Vaclavkova et al., "Oral ponesimod in patients with chronic plaque psoriasis: a randomised, double-blind, placebo-controlled phase 2 trial," Lancet, 2014, 384(9959):2036-45.
Valdimarsson et al., "Psoriasis—as an autoimmune disease caused by molecular mimicry," Trends in Immunology, Oct. 2009, 30(10):494-501.
Variankaval and Cote, "From form to function: Crystallization of active pharmaceutical ingredients," AIChe Journal, Jul. 2008, 54(7): 1682-1688.
Vavricka et al., "Extraintestinal manifestations of inflammatory bowel disease," Inflammatory Bowel Diseases, 2015, 21(8):1982-1992.
Villullas et al., "Characterisation of a Sphingosine 1-Phosphate-Activated Ca2+ Signalling Pathway in Human Neuroblastoma Cells," J. Neurosci. Res, 73:215-226, 2003.
Vippagunta, et al., "Crystalline Solids," Adv. Drug Delivery Rev., 48:3-26 (2001).
Von den Driesch, "Pyoderma gangrenosum: a report of 44 cases with follow-up," Br. J. Dermatol, 1997, 137(6):1000-5.
Webb et al., "Sphingosine 1-phosphate receptors agonists attenuate relapsing-remitting experimental autoimmune encephalitis in SJL mice," J Neuroimmunol., 2004, 153:108-121.
Webster, "The Pathophysiology of Acne," Cutis, 2005, 76(suppl. 2):4-7.
Weenig et al., "Skin ulcers misdiagnosed as pyoderma gangrenosum," N Engl J Med, 2002, 347:1412-1418.
Whetzel et al., "Sphingosine-1 Phosphate Prevents Monocyte/Endothelial Interactions in Type 1 Diabetic NOD Mice Through Activation of the S1P1 Receptor," Circ. Res., 2006, 99:731-739.
Wikipedia [online], "Fingolimod," last edited on Feb. 5, 2022, retrieved on Mar. 23, 2022, retrieved from URL <https://en.wikipedia.org/wiki/Fingolimod>, 7 pages.
Wollina, "Pyoderma gangrenosum—a review," Orphanet Journal of Rare Diseases; 2007, 2:19.
World IBD Day [online], "World IBD Day," 2019, retrieved on Aug. 20, 2019, retrieved from URL <https://worldibdday.org/>, 6 pages.
Xu et al., "Safety, pharmacokinetics, pharmacodynamics, and bioavailability of GSK2018682, a sphingosine-1-phosphate receptor modulator, in healthy volunteers," Am College of Clinical Pharm, 2014, 3(3): 170-178.
Yamamoto, "Crohn's disease and mucocutaneous conditions," Journal of Clinical and Experimental Dermatology Research, 2014 4(2):1-6.
Yan et al., "Discovery of 3-arylpropionic acids as potent agonists of sphingosine-1-phosphate receptor-1 (S1P1) with high selectivity against all other known SIP receptor subtypes," Bioorg. Med. Chem. Lett., 2006, 16:3679-3683.
Yanagawa et al., "FTY720, a Novel Immunosuppressant, Induces Sequestration of Circulating Mature Lymphocytes by Acceleration of Lymphocyte Homing in Rats. II. FTY720 Prolongs Skin Allograft Survival by Decreasing T Cell Infiltration into Grafts But not cytokine production in vivo," J Immunol., 1998, 160:5493-5499.
Yang et al., "Sphingosine kinase/sphingosine 1-phosphate (S1P)/S1P receptor axis is involved in liver fibrosis-associated angiogenesis," J Hepatol., 2013, 59(1):114-23.
Yang et al., "The immune modulator FYT720 prevents autoimmune diabetes in nonobese diabetic mice," Clin. Immunol., 2003, 107:30-35.
Yates et al., "Further evidence for an association between psoriasis, Crohn's disease and ulcerative colitis," Br J Dermatol, 1982, 106(3):323-330.
Zhang et al., "FTY720 attenuates accumulation of EMAP-II+ and MHC-II+ monocytes in early lesions of rat traumatic brain injury," J Cell Mol Med., 2007, 11(2):307-314.
Zhang et al., "FTY720: A Most Promising Immunosuppressant Modulating Immune Cell Functions," Mini Rev. Med Chem., 2007, 7:845-850.
Zhu et al, "Synthesis and Mode of Action of 125I-and 3H-Labeled Thieno[2,3-c]pyridine Antagonists of Cell Adhesion Molecule Expression," J. Org. Chem., 2002, 67(3):943-948.

COMPOUNDS AND METHODS FOR TREATMENT OF INFLAMMATORY BOWEL DISEASE WITH EXTRA-INTESTINAL MANIFESTATIONS

FIELD OF THE INVENTION

The present invention relates to, inter alia, methods of treatment and combinations of (R)-2-(7-(4-cyclopentyl-3-(trifluoromethyl)benzyloxy)-1,2,3,4-tetrahydrocyclopenta[b]indol-3-yl)acetic acid (Compound 1) useful for the treatment of extra-intestinal manifestations (EIM) in an individual with inflammatory bowel disease (IBD) and for the treatment of pyoderma gangrenosum (PG). In some embodiments, the methods further comprise administering Compound 1, or a pharmaceutically salt, solvate, or hydrate thereof, in combination with a therapeutically effective amount of a compound selected from the group consisting of: a corticosteroid, a 5-aminosalicylic acid derivative, and a TNF-alpha inhibitor; or a corticosteroid, an immunosuppressant, a biologic, an anti-inflammatory agent, and an antibiotic.

BACKGROUND OF THE INVENTION

The sphingosine-1-phosphate (SIP) receptors 1-5 constitute a family of G protein-coupled receptors with a seven-transmembrane domain. These receptors, referred to as $S1P_1$ to $S1P_5$ (formerly termed endothelial differentiation gene (EDG) receptor-1, -5, -3, -6, and -8, respectively; Chun et. al., Pharmacological Reviews, 54:265-269, 2002), are activated via binding by sphingosine-1-phosphate, which is produced by the sphingosine kinase-catalyzed phosphorylation of sphingosine. $S1P_1$, $S1P_4$, and $S1P_5$ receptors activate Gi but not Gq, whereas $S1P_2$ and $S1P_3$ receptors activate both Gi and Gq. The $S1P_3$ receptor, but not the $S1P_1$ receptor, responds to an agonist with an increase in intracellular calcium.

The compound (R)-2-(7-(4-cyclopentyl-3-(trifluoromethyl)benzyloxy)-1,2,3,4-tetrahydrocyclopenta[b]indol-3-yl)acetic acid (Compound 1) is a potent ($EC_{50}$ cAMP, 0.093 nM (human)) and selective ($EC_{50}$ β-arrestin, 6.10 nM ($S1P_1$), >10,000 nM ($S1P_2$), >10,000 nM, ($S1P_3$), 147 nM ($S1P_4$), and 24.4 nM ($S1P_5$)), orally available investigational drug candidate for the $S1P_1$ receptor.

In preclinical studies, Compound 1 showed calculated lymphocyte lowering $IC_{50}$ values in four different species: 0.101 μM (mouse), 0.051 μM (rat), 0.058 μM (dog), and 0.098 μM (monkey). Notably, the calculated lymphocyte lowering $IC_{50}$ values reflect total plasma concentration wherein Compound 1 is highly protein bound (97.8% human, 98.0% rat). Compound 1 was shown to be efficacious in the murine experimental autoimmune encephalomyelitis (EAE) model that mimics multiple sclerosis. Prophylactically, Compound 1 prevented the onset and severity of disease relative to vehicle up to day 25, at which time dosing was discontinued. All treatment arms went on to develop severe disease. Therapeutic administration of Compound 1 was also examined. Treatment began at day 18, by which time all animals had developed severe disease. Compound 1 was administered from day 18 to day 37 and showed to reverse the disease relative to vehicle and was similar to the efficacy observed with fingolimod (i.e., GILENYA® was approved in September 2010 for the treatment of individuals with relapsing forms of multiple sclerosis). Similarly, Compound 1 was efficacious in a collagen induced arthritis (CIA) model. Prophylactic oral administration in female Lewis rats resulted in a significant reduction in ankle diameters on day 17 following a daily oral dose and was similar to that observed in rats treated with fingolimod or methotrexate. Improvement in histological parameters in the knees and ankles of CIA rats was also observed, suggesting that inhibiting lymphocyte entry into arthritic joints with Compound 1 treatment suppresses CIA in rodents. Additional details can be found in the following, PCT application, serial number PCT/US2009/004265, filed 22 Jul. 2009 (International Publication Number WO2010/011316); PCT application, serial number PCT/US2011/000153, filed 27 Jan. 2011 (International Publication Number WO2011/094008); and Buzard: D. J., et. al., ACS Med. Chem. Lett. 2014, 5, 1313-1317; each hereby incorporated by reference in its entirety.

S1P is a signaling sphingolipid required by lymphocytes to exit the lymphoid tissue and enter the bloodstream via a chemotactic gradient. The S1P1 receptor is a physiological mediator which has been shown to regulate lymphocyte recirculation between lymphoid tissue and blood. Binding and internalization of the S1P1 receptor may result in lymphocyte retention within lymphoid tissue, with subsequent reduction in peripheral lymphocyte count and lymphocyte availability for recruitment to sites of inflammation. S1P1 receptor surface expression is required for S1P gradient-mediated lymphocyte migration out of lymphoid tissue into the circulation (Brinkmann V., Nat Rev Drug Discov 2010 November; 9(11):883-97).

Compound 1 is an orally available, selective, sphingosine 1-phosphate receptor (S1P) agonist. The S1P1 receptor is a physiological mediator which has been shown to regulate lymphocyte recirculation between lymphoid tissue and blood. Binding and internalization of the S1P1 receptor may result in lymphocyte retention within lymphoid tissue, with subsequent reduction in peripheral lymphocyte count and lymphocyte availability for recruitment to sites of inflammation. S1P1 receptor surface expression is required for S1P gradient-mediated lymphocyte migration out of lymphoid tissue into the circulation (Brinkmann V., et. al., Nat Rev Drug Discov 2010 November; 9 (11):883-97).

Compound 1 is being developed to treat autoimmune diseases. Initial investigations will focus on Inflammatory Bowel Disease (IBD), which is a broad term that describes conditions with chronic or recurring immune response and inflammation of the gastrointestinal tract (Centers for Disease Control and Prevention. Inflammatory bowel disease (IBD). http://www.cdc.gov/ibd/. Accessed Jan. 8, 2015). There are two major types of IBD: Crohn's disease (CD) and ulcerative colitis (UC). These are chronic remittent or progressive inflammatory conditions that may affect the entire gastrointestinal tract (CD) and the colonic mucosa (UC), and are associated with an increased risk for colon cancer. 11 Collectively, individuals with IBD suffer from a multitude of GI symptoms, including diarrhea, rectal bleeding and abdominal pain.

The causes of these IBDs are not completely understood, but three characteristics define their etiology: (1) genetic predisposition; (2) an altered, dysregulated immune response; and (3) an altered response to gut microorganisms. 2 The triggering event for the activation of the immune response in IBD has yet to be identified, but possible factors related to this event include a pathogenic organism (as yet unidentified) or an inappropriate response to a normally innocuous microbial or other antigen (perhaps due to failure to downgrade the inflammatory response, and/or to repeated exposure to such antigen from an alteration in barrier function) (Centers for Disease Control and Prevention.

Inflammatory bowel disease (IBD). http://www.cdc.gov/ibd/. Accessed Jan. 8, 2015). Once the inflammation has been triggered, it may be difficult for the IBD individual's immune system to turn off the response (Danese S. and Fiocchi C., *N Engl J Med.* 2011 November; 365; 18:1713-1725).

The number of individuals diagnosed with IBD has dramatically increased worldwide over the past 50 years.5 In 2014, The Crohn's and Colitis Foundation of American estimated that approximately 1.6 million people are affected by IBD in the United States (US) alone, (Crohn's and Colitis Foundation of America. The Facts About Inflammatory Bowel Diseases. November 2014, New York, NY 10017. http://www.ccfa.org/assets/pdfs/ibdfactbook.pdf. Accessed Jan. 7, 2015) with as many as 70,000 new cases diagnosed in the US each year (Loftus E. V., *Gastroenterology,* 2004; 126:1504-17). In Europe, an estimated 2.5-3 million people are affected by IBD, (Burisch J, et. al., *J Crohns Colitis.* 2013 May; 7(4):322-37) and as many as 5 million may be affected worldwide (World IBD Day. http://www.worldibdday.org/index.html. Accessed Jan. 7, 2015). Universally, incidence rates for both Crohn's disease and ulcerative colitis were highest among individuals between 20 and 40 years old. Thus, IBD affects individuals in the healthiest and productive years of life, resulting in long-term cost to the individual, health-care system and society (American Gastroenterological Assoc. IBD emerges as a global disease, 2012 Jan. 5, ScienceDaily. www.sciencedaily.com/releases/2012/01/120104135402.htm. Accessed Jan. 7, 2015).

Treatment for individuals with IBD is generally for symptomatic care (relief of symptoms) and mucosal healing and includes 5 major classes of medications: aminosalicylates (5-ASA), antibiotics, corticosteroids, immunomodulators, and biologic therapies. These drugs are generally prescribed in a "step-up" approach, with escalation of the medical regimen until a response is achieved (Medscape. Inflammatory Bowel Disease: Practice Essentials. http://emedicine.medscape.com/article/179037-overview#aw2aab6b2b4. Accessed Jan. 8, 2015).

A single ascending dose study and a multiple ascending dose study, conducted in healthy subjects, have demonstrated the lymphocyte lowering capabilities of Compound 1. Lymphocyte trafficking agents such as natalizumab and vedolizumab, both injectable or infused therapies, have demonstrated efficacy in IBD indications. More recently, ozanimod, an S1P1 oral receptor modulator showed promising results in a Phase 2 study for UC. The availability of oral lymphocyte trafficking agents such as Compound 1 would offer individuals an additional, more convenient treatment for IBD.

Inflammatory bowel diseases are associated with various extra-intestinal manifestations (EIMs). The prevalence of IBD with EIMs as co-morbidities varies from 25% to 40% depending on the clinical presentation (Taverela V. F., *Aliment Pharmacol Ther* 2004; Suppl 4:50-53). Specifically, IBD with EIMs could have a negative impact on disease prognosis and quality of life, and in most cases their clinical course becomes independent of gut disease activity.

IBD with skin EIMs is common, occurring in 2% to 34% of the IBD population (Taverela V. F., *Aliment Pharmacol Ther* 2004; Suppl 4:50-53). Specifically, erythema nodosum and pyoderma gangrenosum are the most common skin manifestations of IBD, while psoriasis is the active dermatological comorbidity disease observed most often, affecting 7%-11% of the IBD population (Danese S., et. al., *Br J Dermatol,* 1982; 106: 323-330). IBD and these major skin EIMs in IBD share some common pathogenic mechanisms including neutrophil and lymphocyte infiltration (Marzano A. V., et. al., *Inflamm. Bowel Dis.* 2014; 20:213-227). To this point, targeted immunosuppressive therapies have demonstrated efficacy in IBD with skin EIMs. For example, TNF-alpha inhibitors are known to reduce intestinal inflammation and induce clinical remission in individuals with IBD, and are also known to reduce EIMs of IBD. However, a small percentage of individuals with IBD taking TNF-alpha inhibitors experience de novo paradoxical psoriasis (reporting a rate ranging from 1.6 to 8.8%) despite beneficial intestinal effects while on treatment (Freling E., et. al., *Am J Gastroenterol* 2015; 110:1186-1196). The pathophysiology of the paradoxical disease is not understood, but the leading hypothesis is that decreased TNF-alpha induces the activation of autoreactive T cells and an increased interferon activity as well as other pro-inflammatory cytokines, such as IL-12, IL-17, IL-23. Recently, interferon-alpha (IFN-alpha) production by dermal plasmacytoid dendritic cells (DCs) has been identified as a key element in the early phase of psoriatic skin lesion induction. Plasmacytoid DCs, the natural IFN-alpha producing cells, have recently been shown to infiltrate the skin of individuals with psoriasis and to produce IFN-alpha. IFN-alpha induces the expression of CXCR3 on T cells, facilitating homing to the skin (Nestle F. O., et. al., *J Exp Med.* 2005 Jul. 4; 202(1):135-43).

It is clear that existing treatments for IBD, and IBD skin EIMs, including TNF-alpha inhibitors, have limitations and a need remains for therapies with sustained efficacy, improved safety, and convenient administration (Paul C., et. al., *J Eur Acad Dermatol Venereol* 2012; 26 (suppl 3): 1-10).

Spingosine-1-phosphate (S1P) is a spingolipid required by lymphocytes to exit the lymphoid tissue and enter the bloodstream via a chemotactic gradient. Agonists of the S1P receptor-1 (S1P1) block lymphocyte migration out of the lymph tissue through internalization of the receptor, resulting in a sequestration of lymphocytes (Brinkmann V., et. al., *J Biol Chem* 2002; 277:21453-57). Recent clinical development of S1P1 agonists and the resulting lymphocyte sequestration have potential for treating multiple autoimmune and chronic inflammatory diseases including multiple sclerosis, IBD and psoriasis. Fingolimod was the first drug in this class to be approved the treatment of multiple sclerosis (Kappos L, et. al., *N Engl J Med.* 2010 Feb. 4; 362(5):387-401). More recently the S1P1 receptor agonist ponesimod was observed to reduce the severity of chronic plaque psoriasis after chronic oral administration in a phase 2 randomized clinical trial (Vaclavkova A., et. al., *Lancet* 2014; 384: 2036-45). In this study, ponesimod was associated with dyspnea, elevated liver enzymes, bradycardia, headache and dizziness. Furthermore, S1P1 agonists (FTY720, SEW2871) have been observed to have an anti-inflammatory impact on the production of IL-12 family cytokines, indicating therapeutic potential for S1P treatment of several inflammatory diseases like psoriasis (Schaper K., et. al., *Mol Immunol.* 2014 May; 59(1):10-8). Importantly, a recent report demonstrating S1P4 agonists inhibit plasmacytoid dendritic cell activation and interferon-alpha production suggest a potential therapeutic role for S1P1/S1P4 agonists like Compound 1 in paradoxical psoriasis (Dillmann C., et. al., *J Immunol.* 2016 Feb. 15; 196(4):1579-90).

Pyoderma gangrenosum (PG) is considered to be a rare disorder associated with inflammation, mainly characterized by large skin ulcers (Cohen, P. R., *Am J Clin Dermatol.* 2009; 10(5):301-12; Marzano A. V., et. al., *Clinical and Experimental Immunology,* 2010; 162: 1-11). The ulcers are known to break down at a rapid rate and are painful, often turning necrotic (Su W., et. al., *J Cut. Path;* 1986; 13:

323-330). Other inflammatory diseases such as inflammatory bowel disorder (IBD), ulcerative colitis (UC) and Bechet's disease are indicated to share the same clinicopathophysiology (Gameiro A, et. al., *Clin. Cos. Inv. Dermatol;* 2015; 8: 285-293). PG was considered to have a parallel relationship with other underlying diseases (e.g., UC, IBD) with PG being the cutaneous manifestation (Brunsting L A, et. al. *Arch Dermatol Syph;* 1930; 22:655-680), however this hypothesis was drawn into question by Driesch (Von den Driesch P., *Br. J. Dermatol;* 1997; 137 (6):1000-5) and published data suggesting consideration of PG as an independent disease, irrespective of underlying disorders.

Based upon U.S. Department of Health and Human Services' National Institutes of Health's Office of Rare Disease Research, the incidence of PG has been estimated that each year in the United States, 1 person per 100,000 people is affected (U.S. Department of Health & Human Services National Institutes of Health, https://rarediseases.info.nih.gov/diseases/7510/pyoderma-gangrenosum). The incidence peak occurs between the ages of 20 to 50 years, with women being more often affected than men (Wollina U., *Orphanet Journal of Rare Diseases;* 2007, 2:19).

Diagnosis of PG is reliant on clinical signs, exclusion principle and supported by histopathology of the biopsy (Wollina U., *Orphanet Journal of Rare Diseases;* 2007, 2:19; Weenig R. H., et. al., *N Engl J Med;* 2002; 347:1412-1418). The histopathology can differ dependent on the timing (early stage-mild to moderate perivascular lymphocytic infiltrate; late-stage necrosis with dense lymphocytic infiltration along with involvement of blood vessels) and site of biopsy (Su W., et. al., *J Cut. Path;* 1986; 13: 323-330). The diagnosis using clinical signs alone has been shown historically to lead to misdiagnoses as PG for at least 6 categories including vascular occlusive or venous disease, vasculitis, cancer, infectious disease, exogenous tissue injury and drug reactions (Weenig R. H., et. al., *N Engl J Med;* 2002; 347:1412-1418), and support of exclusion and histopathology is recommended for diagnosis.

The documented treatments for PG include, for example, systemic corticosteroids and cyclosporin A. Combinations of steroids with cytotoxic drugs are used in resistant cases. The combination of steroids with sulfa drugs or immunosuppressants has been used as steroid sparing modalities. In some cases, anti-TNF therapy was reported to be beneficial which suggests that inhibition of TNF may help.

Gevokizumab is a potent IL-1 beta monoclonal antibody with unique allosteric modulating properties and has the potential to treat individuals with a wide variety of inflammatory and other diseases. Gevokizumab binds strongly to interleukin–1 beta (IL-1 beta), a pro-inflammatory cytokine, and modulates the cellular signaling events that produce inflammation. This agent was being developed as a potential treatment for PG; however, development was discontinued in 2016.

Agonists of the S1P1 receptor block lymphocyte migration out of the lymph tissue through internalization of the receptor, resulting in a sequestration of lymphocytes (Brinkmann V., et. al., *J Biol Chem;* 2002; 277:21453-57). Recent clinical development of S1P1 receptor agonists and the resulting lymphocyte sequestration have potential for treating multiple autoimmune and chronic inflammatory diseases including multiple sclerosis, IBD and psoriasis. Fingolimod was the first drug in this class to be approved for the treatment of multiple sclerosis (Kappos L., et. al., *N Engl J Med.;* 2010 Feb. 4; 362(5):387-401). More recently the S1P1 receptor agonist ponesimod was observed to reduce the severity of chronic plaque psoriasis after chronic oral administration in a Phase 2 randomized clinical trial (Vaclavkova A., et. al., *Lancet;* 2014; 384: 2036-45). In this study, ponesimod was associated with dyspnea, elevated liver enzymes, bradycardia, headache and dizziness. Furthermore, S1P1 agonists (FTY720, SEW2871) have been observed to have an anti-inflammatory impact on the production of IL-12 family cytokines, indicating therapeutic potential for S1P treatment of several inflammatory diseases like psoriasis (Schaper K., et. al., *Mol Immunol.;* 2014 May; 59(1):10-8). Importantly, a recent report demonstrating S1P4 agonists inhibition of plasmacytoid dendritic cell activation and interferon-alpha production suggest a potential therapeutic role for S1P1/S1P4 agonists like Compound 1 in paradoxical psoriasis (Dillmann C., et. al., *Cells. J Immunol.;* 2016 Feb. 15; 196(4):1579-90).

Histopathology of ulcerative pyoderma gangrenosum (PG) is characterized by a dense dermal infiltrate composed mainly of neutrophils in biopsy from the central area of ulceration, and a mainly lymphocytic infiltrate with thrombosis of vessels and extravasated erythrocytes in biopsy from the border of the ulcer (Cohen, P. R., *Am J Clin Dermatol.;* 2009; 10(5):301-12). In individuals with ulcerative PG the number of T-lymphocytes are significantly higher at the wound edge compared to the wound bed. In contrast, neutrophils were significantly more numerous in the wound bed than the wound edge (Marzano A. V., et. al., *Experimental Immunology,* 2010; 162: 1-11). This suggests that activated T-lymphocytes at the wound edge could promote ulcer formation. Further support for T-cell involvement in the disease comes from observations in individuals with PG that are characterized by an over-expression in the blood of the CD4+CCR5+ and CD4+CCR6+ and a down-regulation of CD4+CCR4+ counts with respect to healthy subjects (Quaglino P, et. al., *J Eur Acad Dermatol Venereol;* 2016; 30: 655-8).

In addition to the potential anti-inflammatory benefits of systemic lymphocyte immunomodulation, S1P is known to exert anti-proliferative effects in human keratinocytes (Schuppel M., et. al., *J Invest Dermatol* 2008; 128:1747-56), and inhibits dendritic cell migration (Reines I., et. al., *J Clin Invest Dermatol* 2009; 129:1954-62). Thus, the potential role of S1P receptor modulation in skin EIMs of IBD might involve both systemic and local epidermal mechanisms.

Further, a differentiated profile for Compound 1 compared to other S1P modulators for the treatment of PG could arise from the hypothesis that S1P4 as well as S1P1 receptor modulation could aid in neutrophil trafficking (Allende M. L., *J Biol Chem;* 2011; 286: 7348-58).

Next generation S1P modulators, such as, (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, would offer a novel therapy for IBD individuals with skin EIMs.

Further, the evidence suggests that T-lymphocytes can play a role in PG and that reduction of lymphocytes by S1P1 receptor modulators represent a novel therapeutic approach in PG. The availability of lymphocyte trafficking agents, such as, (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, would offer individuals a novel therapy for pyoderma gangrenosum.

SUMMARY OF THE INVENTION

In its various embodiments, the present invention is directed to, inter alia, methods of treating active skin extraintestinal manifestations (EIM) in an individual with inflammatory bowel disease (IBD) in need thereof comprising administering a therapeutically effective amount of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof.

In other embodiments, the present invention is directed to uses of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of active skin extra-intestinal manifestations (EIM) in an individual with inflammatory bowel disease (IBD).

In some embodiments, the individual has at least one condition selected from the group consisting of: psoriasis, erythema nodosum (EN), and pyoderma gangrenosum (PG).

In some embodiments, the individual has psoriasis.

In some embodiments, the individual has erythema nodosum (EN).

In some embodiments, the individual has pyoderma gangrenosum (PG).

In some embodiments, the individual has at least one condition selected from the group consisting of: psoriasis, erythema nodosum (EN), and pyoderma gangrenosum (PG).

In some embodiments, the skin extra-intestinal manifestations (EIM) is psoriasis.

In some embodiments, the skin extra-intestinal manifestations (EIM) is erythema nodosum (EN).

In some embodiments, the skin extra-intestinal manifestations (EIM) is pyoderma gangrenosum (PG).

In some embodiments, the Compound 1, or a pharmaceutically acceptable salt, hydrate, or solvate thereof, is in an amount equivalent to about 1 mg to about 5 mg of Compound 1.

In some embodiments, the Compound 1, or a pharmaceutically acceptable salt, hydrate, or solvate thereof, is in an amount equivalent to about 2 mg of Compound 1.

In some embodiments, the Compound 1, or a pharmaceutically acceptable salt, hydrate, or solvate thereof, is selected from: Compound 1, a calcium salt of Compound 1, and an L-arginine salt of Compound 1.

In some embodiments, the Compound 1, or a pharmaceutically acceptable salt, hydrate, or solvate thereof, is an L-arginine salt of Compound 1.

In some embodiments, the Compound 1, or a pharmaceutically acceptable salt, hydrate, or solvate thereof, is an anhydrous, non-solvated crystalline form of the L-arginine salt of Compound 1.

In some embodiments, the Compound 1, or a pharmaceutically acceptable salt, hydrate, or solvate thereof, is a crystalline free-plate habit of the non-solvated L-arginine salt of Compound 1.

In some embodiments, the Compound 1, or a pharmaceutically acceptable salt, hydrate, or solvate thereof, is an anhydrous, non-solvated crystalline form of Compound 1.

In some embodiments, the Compound 1, or a pharmaceutically acceptable salt, hydrate, or solvate thereof, is administered orally.

In some embodiments, the Compound 1, or a pharmaceutically acceptable salt, hydrate, or solvate thereof, is formulated as a capsule or tablet suitable for oral administration.

In some embodiments, the methods further comprise administering Compound 1, or a pharmaceutically salt, solvate, or hydrate thereof, in combination with a therapeutically effective amount of a compound selected from the group consisting of: a corticosteroid, a 5-aminosalicylic acid derivative, and a TNF-alpha inhibitor.

In some embodiments, the corticosteroid is cortisone, dexamethasone, hydrocortisone, methylprednisolone, prednisolone, prednisone, triamcinolone, and fludrocortisone.

In some embodiments, the 5-aminosalicylic acid derivative is selected from the group consisting of: balsalazide, mesalamine, olsalazine, and sulfasalazine.

In some embodiments, the TNF-alpha inhibitor is selected from the group consisting of: as infliximab (Remicade®), adalimumab (Humira®), certolizumab pegol (Cimzia®), and golimumab (Simponi®), and etanercept (Enbrel®).

In further embodiments, the present invention is directed to, inter alia, methods of treating pyoderma gangrenosum (PG) in an individual in need thereof comprising administering a therapeutically effective amount of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof.

In other embodiments, the present invention is directed to uses of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of pyoderma gangrenosum (PG).

In some embodiments, the individual has at least one condition selected from the group consisting of: an inflammatory bowel disease, arthritis, a hematological disease, and an autoinflammatory disease.

In some embodiments, the individual has at least one condition selected from the group consisting of: ulcerative colitis and Crohn's disease.

In some embodiments, the individual has at least one condition selected from the group consisting of: rheumatoid arthritis and seronegative arthritis.

In some embodiments, the individual has at least one condition selected from the group consisting of: myelocytic leukemia, hairy cell leukemia, myelofibrosis, myeloid metaplasia, and monoclonal gammopathy.

In some embodiments, the individual has at least one condition selected from the group consisting of: PAPA syndrome and granulomatosis with polyangiitis.

In some embodiments, the Compound 1, or a pharmaceutically acceptable salt, hydrate, or solvate thereof, is in an amount equivalent to about 1 mg to about 5 mg of Compound 1.

In some embodiments, the Compound 1, or a pharmaceutically acceptable salt, hydrate, or solvate thereof, is in an amount equivalent to about 2 mg of Compound 1.

In some embodiments, the Compound 1, or a pharmaceutically acceptable salt, hydrate, or solvate thereof, is selected from: Compound 1, a calcium salt of Compound 1, and an L-arginine salt of Compound 1.

In some embodiments, the Compound 1, or a pharmaceutically acceptable salt, hydrate, or solvate thereof, is an L-arginine salt of Compound 1.

In some embodiments, the Compound 1, or a pharmaceutically acceptable salt, hydrate, or solvate thereof, is an anhydrous, non-solvated crystalline form of the L-arginine salt of Compound 1.

In some embodiments, the Compound 1, or a pharmaceutically acceptable salt, hydrate, or solvate thereof, is a crystalline free-plate habit of the non-solvated L-arginine salt of Compound 1.

In some embodiments, the Compound 1, or a pharmaceutically acceptable salt, hydrate, or solvate thereof, is an anhydrous, non-solvated crystalline form of Compound 1.

In some embodiments, the Compound 1, or a pharmaceutically acceptable salt, hydrate, or solvate thereof, is administered orally.

In some embodiments, the Compound 1, or a pharmaceutically acceptable salt, hydrate, or solvate thereof, is formulated as a capsule or tablet suitable for oral administration.

In some embodiments, the methods further comprise administering Compound 1, or a pharmaceutically salt, solvate, or hydrate thereof, in combination with a therapeutically effective amount of a compound selected from the group consisting of: a corticosteroid, an immunosuppressant, a biologic, an anti-inflammatory agent, and an antibiotic.

In some embodiments, the corticosteroid is cortisone, dexamethasone, hydrocortisone, methylprednisolone, prednisolone, prednisone, triamcinolone, and fludrocortisone.

In some embodiments, the immunosuppressant is selected from the group consisting of: cyclosporin A, tacrolimus, and mycophenolic acid.

In some embodiments, the immunosuppressant is cyclosporin A.

In some embodiments, the biologic is selected from the group consisting of: abatacept, adalimumab, adalimumab-atto, anakinra, certolizumab pegol, etanercept, etanercept-szzs, golimumab, infliximab, infliximab-dyyb, rituximab, tocilizumab, tofacitinib, vedolizumab, and natalizumab.

In some embodiments, the anti-inflammatory agent is selected from the group consisting of: aceclofenac, vedolizumab, aspirin, celecoxib, clonixin, dexibuprofen, dexketoprofen, diclofenac, diflunisal, droxicam, enolic acid, etodolac, etoricoxib, fenoprofen, flufenamic acid, flurbiprofen, ibuprofen, indomethacin, ketoprofen, ketorolac, licofelone, lornoxicam, loxoprofen, meclofenamic acid, mefenamic acid, meloxicam, nabumetone, naproxen, oxaprozin, parecoxib, phenylbutazone, piroxicam, salicylic acid, salsalate, sulindac, tenoxicam, tolfenamic acid, and tolmetin.

In some embodiments, the antibiotic is selected from the group consisting of: ceftobiprole, ceftaroline, clindamycin, dalbavancin, daptomycin, fusidic acid, linezolid, mupirocin, oritavancin, tedizolid, telavancin, tigecycline, vancomycin, amikacin, gentamicin, kanamycin, neomycin, netilmicin, tobramycin, and paromomycin.

In some embodiments, the antibiotic is selected from the group consisting of: mupirocin and gentamicin.

These and other aspects of the invention disclosed herein will be set forth in greater detail as the patent disclosure proceeds.

DETAILED DESCRIPTION OF THE INVENTION

Figure 1:
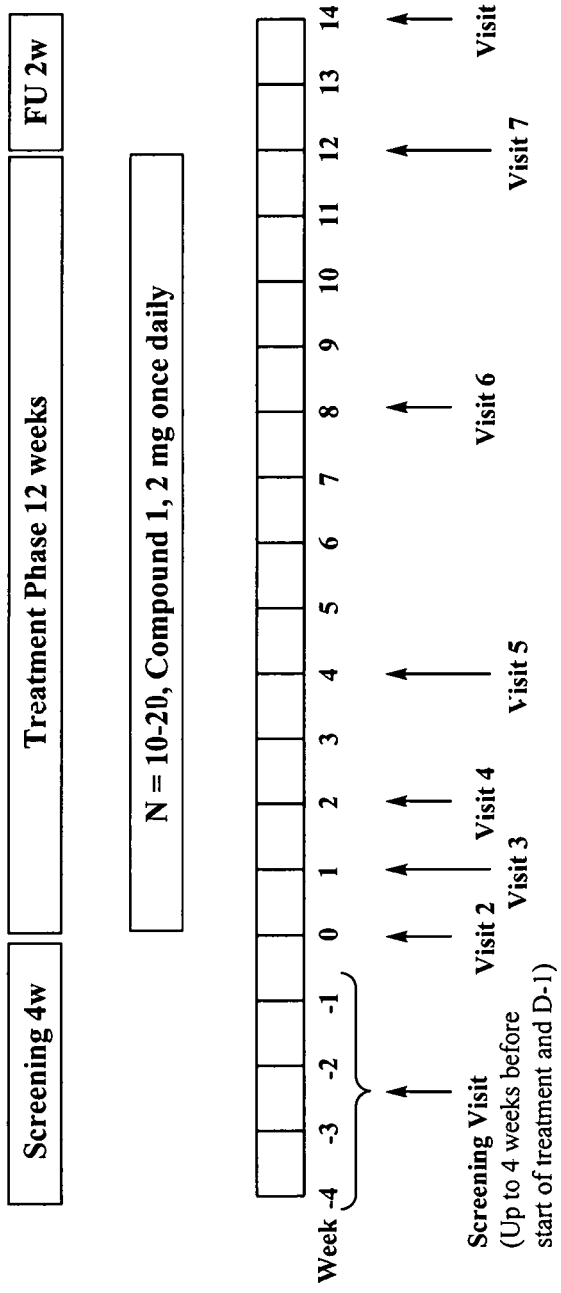
FIG. 1 shows a clinical protocol for the treatment of IBD with skin EIMs with Compound 1.
Figure 2:
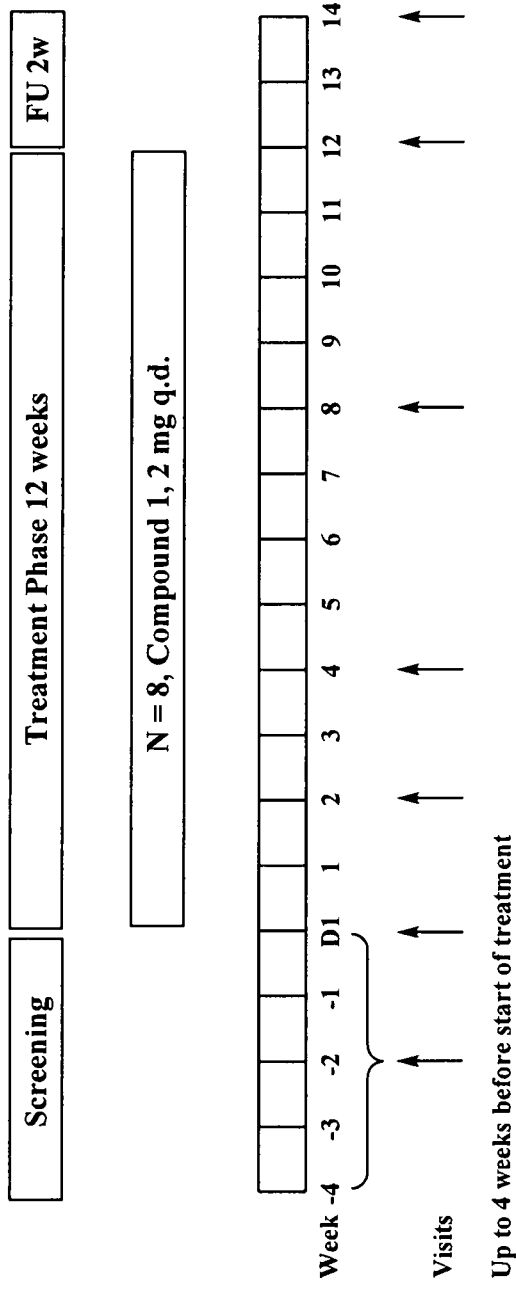
FIG. 2 shows a clinical protocol for the treatment of pyoderma gangrenosum (PG) with Compound 1.

In its various embodiments, the present invention is directed to, inter alia, methods of treating active skin extra-intestinal manifestations (EIM) in an inflammatory bowel disease (IBD) individual in need thereof comprising administering a therapeutically effective amount of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof.

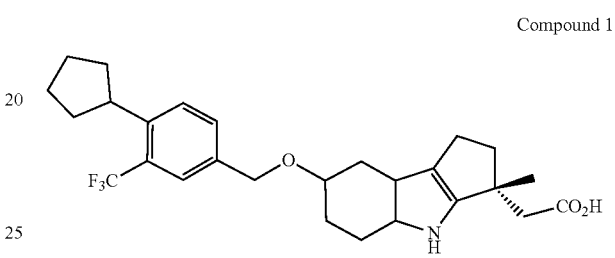

Compound 1

In other embodiments, the present invention is directed to uses of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of extra-intestinal manifestations (EIM) in an individual with inflammatory bowel disease (IBD).

In other embodiments, the present invention is directed to (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, for use in the treatment of extra-intestinal manifestations (EIM) in an individual with inflammatory bowel disease (IBD).

In some embodiments, the EIM is a dermal EIM. In some embodiments, the EIM is an active skin EIM.

The present invention further provides, inter alia, methods of treating pyoderma gangrenosum (PG) in an individual in need thereof comprising administering a therapeutically effective amount of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof.

In other embodiments, the present invention is directed to uses of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of pyoderma gangrenosum (PG) in an individual.

In other embodiments, the present invention is directed to (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, for use in the treatment of pyoderma gangrenosum.

Certain processes for the preparation of Compound 1 and the L-arginine salt of Compound 1 have been previously described; see WO2010/011316 and WO2011/094008. In addition, the novel crystalline plate habit for the L-arginine salt of Compound 1 has been previously described and is referred to herein as, "crystalline free-plate habit of the non-solvated L-arginine salt of Compound 1"; see WO2016/209809.

The following is a list of abbreviations: ACS (acute coronary syndrome); ADL (activities of daily living); AE (adverse event); ALB (albumin); ALK-P (alkaline phosphatase); ALT (alanine aminotransferase (SGPT)); AST (aspartate aminotransferase (SGOT)); bpm (beats per minute); BUN (blood urea nitrogen); Ca (calcium); CBC (complete blood count); CFR (Code of Federal Regulations); CI (confidence interval); CIA (collagen-induced arthritis); Cl (chloride); CL/F (apparent oral clearance); CMO (contract manufacturing organization); CRF (case report form); CRF (case report form); CRO (contract research organization); CRP (C-reactive protein); D (day); DLQI (Dermatology Life Quality Index); EAE (experimental autoimmune encephalomyelitis); ECG (electrocardiogram); ED50 (median effective dose); EIM (extra-intestinal manifestation); ELISA (enzyme-linked immunosorbent assay); EOS (end of study); EOT (end of treatment); FDA (Food and Drug Administration); FEF25-75% (mean forced expiratory flow between 25 and to 75% of FVC); FEV1 (forced expiratory volume in the first second); FU (follow-up); FVC (forced vital capacity); GCP (Good Clinical Practice); GGT (gamma glutamyl transferase); h (hour); Hb (hemoglobin); HBsAg (hepatitis B surface antigen); hCG (human chorionic gonadotropin); Hct (hematocrit); HCV (hepatitis C virus); HDPE (High-density polyethylene); HIV (human immunodeficiency virus); HR (heart rate); HREC (human resource ethics committee (AUS)); IBD (Inflammatory Bowel Disease); IBDQ (Inflammatory Bowel Disease Questionnaire); IBDQ (Inflammatory Bowel Disease Questionnaire); ICF (informed consent form); ICH (International Conference on Harmonization); IEC (Independent Ethics Committee); IND (Investigational New Drug); INR (international normalized ratio); IRB (Institutional Review Board); IUD (intrauterine device); IUS (hormone-releasing system); kg (kilogram); LDH (lactate dehydrogenase); MCH (mean corpuscular hemoglobin); MCV (mean corpuscular volume); MedDRA (Medical Dictionary for Regulatory Activities); mg (milligram); MI (myocardial infarction); mL (milliliter); mm (millimeter); mmHg (millimeters of mercury); MRSD (maximum recommended starting dose); Na (sodium); NOAEL (no observed adverse effect level); OCT (optical coherence tomography); OTC (over-the-counter); PA (Posteroanterior); PASI (Psoriasis Area and Severity Index); PBL (peripheral blood lymphocyte); PFT (pulmonary function test); PG (pyoderma gangrenosum); PGA (Physicians Global Assessments); PI (Principal Investigator); PPD (A CRO responsible for SAE processing in this study); PPD PVG (A Pharmacovigilance department of PPD); PRO (patient reported outcome); PRO (patient reported outcome); PT (prothrombin time); PTT (partial thromboplastin time); PV (pharmacovigilance); q.d. (quaque die (once daily)); RBC (red blood cell (count)); RT-PCR (real-time polymerase chain reaction); S1P (sphingosine 1-phosphate receptor); S1P(1-5) (sphingosine 1-phosphate (1-5) receptor); SAE (serious adverse event); SAP (statistical analysis plan); SBP (systolic blood pressure); SD (standard deviation); sec (second); SOP(s) (standard operating procedure(s)); $t_{1/2}$ (elimination half-life); TEM (T effector memory cells); TIA (Transient Ischemic Attack); TIA (transient ischemic attack); tmax (the median time to reach maximum plasma concentration; UC (ulcerative colitis); ULN (upper limit of normal); VAS (visual analogue scale); VS (vital signs); VZV (varicella zoster virus); WBC (white blood cell); WHO (World Health Organization); and WHODRUG (World Health Organization Drug Dictionary).

Crystalline L-Arginine Salt of Compound 1

Figure 3:
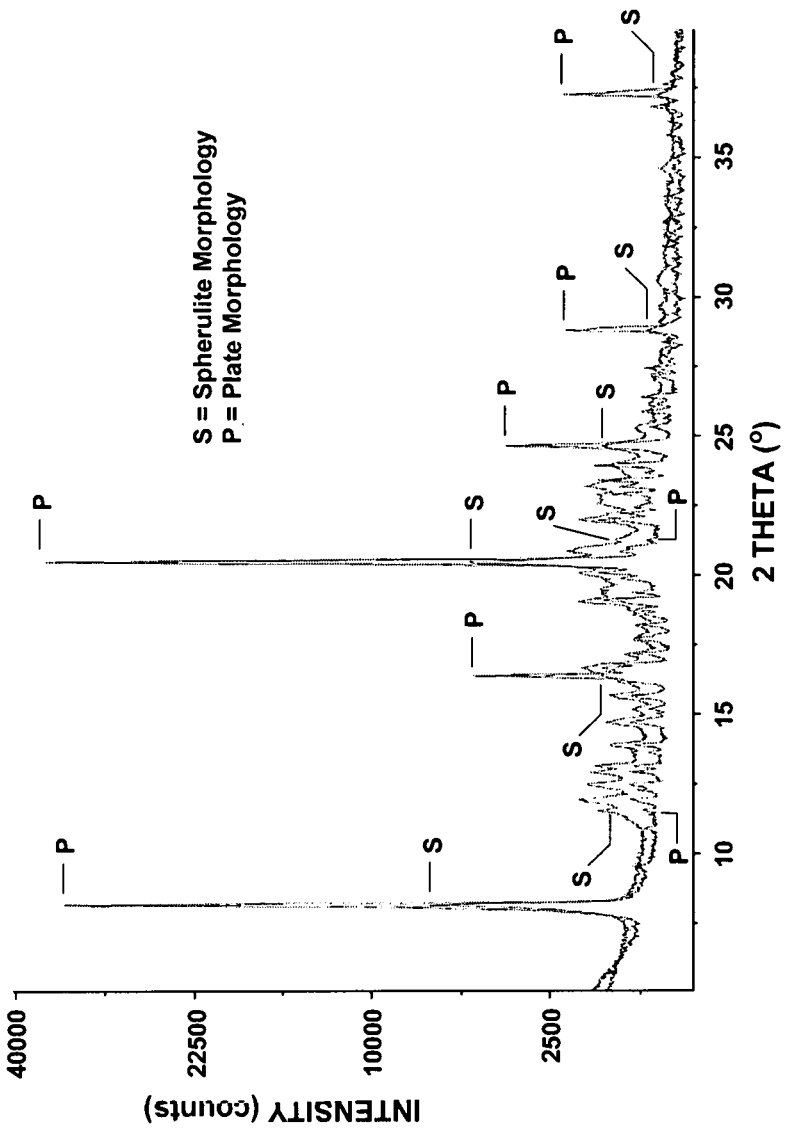
FIG. 3 shows a PXRD Pattern overlay for the L-arginine salt of Compound 1 showing the peak intensity differences between plates and spherulites indicating a higher degree of crystallinity for the plates compared to the spherulites. Also shown is the lower sample-related background scatter (i.e., a lower amorphous halo contribution) for the plates. However, the plates and spherulites are observed to show the same crystal phase.

The crystalline free-plate habit or morphology and processes useful in the preparation of a crystalline free-plate habit of L-arginine salt of (R)-2-(7-(4-cyclopentyl-3-(trifluoromethyl)-benzyloxy)-1,2,3,4-tetrahydrocyclopenta[b]indol-3-yl)acetic acid are described in WO2016/209809. The plates were discovered from the novel synthetic methods and were shown to be thin hexagonal-like plates with two opposite sides of the plate being longer that the other sides (i.e., elongated hexagonal plate). However, due to the thin characteristic of the plates, a complete unbroken plate is rarely seen. Instead, what is generally observed are large to small broken pieces of the thin hexagonal-like plates. It is understood by those skilled in the art that microscopy is one of the more useful techniques to distinguish two crystalline habits or morphologies. This is particularly useful when 2 or more morphologies are associated with the same or substantially the same crystal phase as is the case with the L-arginine salt of Compound 1. Comparing the PXRD patterns of the habit prepared previously (i.e., WO2011/094008 and Example 2 infra) and the plate habit prepared as described in WO2016/209809 (i.e., see FIG. 3, PXRD overlay between spherulites and plates) it was observed that the two PXRD patterns were the same or substantially the same, thus the two habits represented the same crystal phase.

Although the two habits revealed the same or substantially the same PXRD pattern, a higher degree of crystallinity was observed for the plate habit as indicated by substantially higher peak intensities and yet lower sample-related background scatter (i.e., a lower amorphous halo contribution). Since sample size and sample preparation can affect peak intensities and sample-related background scatter, and since the two habits share the same crystal phase, PXRD may not be considered the most appropriate test method to distinguish between two habits. However, PXRD does allow for determining whether two habits have the same crystal phase or different crystal phases. For determining different habits, microscopy is one of the more useful methods. Accordingly, the skilled person would be capable of reviewing a micrograph for a crystal habit and readily determine the crystal habit.

In addition to the techniques recognized in the art, specific surface can also be used to characterize a habit, such as the free-plates. Accordingly, the specific surface area values disclosed in the present invention have been obtained by means of a specific surface area analysis technique based on the BET (Brunauer, Emmett and Teller) theory, which is a well-accepted theory known in the art for the calculation of surface areas of solids by means of measuring their physical adsorption of gas molecules (see: Brunauer, S.; Emmett, P. H.; and Teller, E.; *J. Am. Chem. Soc.,* 1938, 60, 309). In particular, the specific surface area values measured in the present invention have been calculated from the BET surface area plot obtained by measuring the quantity of nitrogen gas molecules adsorbed by a weighted amount of solid at different relative pressures (P/P$_O$) within the range 0.05-0.3 (P/P$_O$), at 77.3 K. The measurement of the adsorption of gas molecules was carried out by means of a Micromeritics™ TriStar II BET surface analyzer having the characteristics as set out below in Example 4. Namely, nitrogen gas was used for the adsorption measurement. The sample for each analysis was degassed at 25° C. for 960 minutes under vacuum (i.e., 100 mm/Hg). The determination of the adsorption of nitrogen was measured at 77.3 K at eleven relative pressures (P/P₀) sufficiently dispersed within the range of about 0.05 to about 0.30 (i.e. eleven absolute pressures in the range of about 36 mm Hg to about 223 mm Hg relative to the saturated pressure at the time of measurement that ranged from about 738 mmHg to about 743 mmHg).

One aspect of the present invention relates to a novel crystalline plate morphology of L-arginine salt of (R)-2-(7-(4-cyclopentyl-3-(trifluoromethyl)benzyloxy)-1,2,3,4-tetrahydrocyclo-penta[b]indol-3-yl)acetic acid as described herein.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclo-penta[b]indol-3-yl)acetic acid.

In some embodiments, the crystalline free-plate habit has a powder X-ray diffraction pattern comprising peaks, in terms of 2θ, at 8.2°±0.2°, 16.4°±0.2°, and 20.5°±0.2°. In some embodiments, the crystalline free-plate habit has a powder X-ray diffraction pattern comprising peaks, in terms of 2θ, at 8.2°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, and 28.8°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°.

In some embodiments, the crystalline free-plate habit has a differential scanning calorimetry trace comprising an endotherm with an extrapolated onset temperature of 205.0° C. to 208.5° C. at a scan rate of 10° C./minute. In some embodiments, the crystalline free-plate habit has a differential scanning calorimetry trace comprising an endotherm with an extrapolated onset temperature of 205.0° C. to 208.1° C. at a scan rate of 10° C./minute. In some embodiments, the crystalline free-plate habit has a differential scanning calorimetry trace comprising an endotherm with an extrapolated onset temperature of 205.5° C. to 208.5° C. at a scan rate of 10° C./minute. In some embodiments, the crystalline free-plate habit has a differential scanning calorimetry trace comprising an endotherm with an extrapolated onset temperature of 206.0° C. to 208.5° C. at a scan rate of 10° C./minute. In some embodiments, the crystalline free-plate habit has a differential scanning calorimetry trace comprising an endotherm with an extrapolated onset temperature of 206.5° C. to 208.5° C. at a scan rate of 10° C./minute. In some embodiments, the crystalline free-plate habit has a differential scanning calorimetry trace comprising an endotherm with an extrapolated onset temperature of 205.5° C. to 208.1° C. at a scan rate of 10° C./minute. In some embodiments, the crystalline free-plate habit has a differential scanning calorimetry trace comprising an endotherm with an extrapolated onset temperature of 206.5° C. to 208.1° C. at a scan rate of 10° C./minute. In some embodiments, the crystalline free-plate habit has a differential scanning calorimetry trace comprising an endotherm with an extrapolated onset temperature of 207.0° C. to 208.1° C. at a scan rate of 10° C./minute.

In some embodiments, the crystalline free-plate habit has a dynamic moisture sorption (DMS) profile with an adsorption phase from 30% RH to 90% RH wherein the crystalline free-plate habit gains about 0.3% weight or less at 90% RH. In some embodiments, the crystalline free-plate habit has a dynamic moisture sorption (DMS) profile with an adsorption phase from 30% RH to 90% RH wherein the crystalline free-plate habit gains about 0.2% weight or less at 90% RH.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclo-penta[b]indol-3-yl)acetic acid having a BET specific surface area of about 0.05 m²/g, about 0.1 m²/g, about 0.15 m²/g, about 0.2 m²/g, about 0.25 m²/g, about 0.3 m²/g, about 0.35 m²/g, about 0.4 m²/g, about 0.45 m²/g, about 0.5 m²/g, about 0.55 m²/g, about 0.6 m²/g, about 0.65 m²/g, or about 0.7 m²/g to about 2.0 m²/g, about 2.5 m²/g, about 3.0 m²/g, about 3.5 m²/g, about 4.0 m²/g, about 4.5 m²/g, about 5.0 m²/g, about 5.5 m²/g, about 6.0 m²/g, about 6.5 m²/g, about 7.0 m²/g, about 7.5 m²/g, about 8.0 m²/g, about 8.5 m²/g, about 9.0 m²/g, or about 9.5 m²/g.

In some embodiments, the crystalline free-plate habit has a BET specific surface area of about 0.1 m²/g to about 5.0 m²/g. In some embodiments, the crystalline free-plate habit has a BET specific surface area of about 0.1 m²/g to about 4.0 m²/g. In some embodiments, the crystalline free-plate habit has a BET specific surface area of about 0.3 m²/g to about 4.0 m²/g. In some embodiments, the crystalline free-plate habit has a BET specific surface area of about 0.5 m²/g to about 4.0 m²/g. In some embodiments, the crystalline free-plate habit has a BET specific surface area of about 0.6 m²/g to about 4.0 m²/g. In some embodiments, the crystalline free-plate habit has a BET specific surface area of about 0.3 m²/g to about 3.0 m²/g. In some embodiments, the crystalline free-plate habit has a BET specific surface area of about 0.4 m²/g to about 2.0 m²/g. In some embodiments, the crystalline free-plate habit has a BET specific surface area of about 0.5 m²/g to about 1.8 m²/g. In some embodiments, the crystalline free-plate habit has a BET specific surface area of about 0.6 m²/g to about 1.6 m²/g.

In some embodiments, the crystalline free-plate habit has:
1) a powder X-ray diffraction pattern comprising peaks, in terms of 2θ, at 8.2°±0.2°, 16.4°±0.2°, 20.50±0.2°, 24.6°±0.2°, 28.8°±0.2°, and 37.3°±0.2°;
2) a differential scanning calorimetry trace comprising an endotherm with an extrapolated onset temperature of 205.0° C. to 208.5° C. at a scan rate of 10° C./minute; and/or
3) a dynamic moisture sorption (DMS) profile with an adsorption phase from 30% RH to 90% RH wherein the crystalline free-plate habit gains about 0.3% weight or less at 90% RH.

In some embodiments, the crystalline free-plate habit has:
1) a powder X-ray diffraction pattern comprising peaks, in terms of 2θ, at 8.2°±0.2°, 16.4°±0.2°, 20.5°±0.2°, and 24.6°±0.2°;
2) a differential scanning calorimetry trace comprising an endotherm with an extrapolated onset temperature of 206.5° C. to t 208.5° C. at a scan rate of 10° C./minute; and/or
3) a dynamic moisture sorption (DMS) profile with an adsorption phase from 30% RH to 90% RH wherein the crystalline free-plate habit gains about 0.3% weight or less at 90% RH.

In some embodiments, the crystalline free-plate habit has:
1) a powder X-ray diffraction pattern comprising peaks, in terms of 2θ, at 8.2°±0.2°, 20.5°±0.2°, and 24.6°±0.2°;
2) a differential scanning calorimetry trace comprising an endotherm with an extrapolated onset temperature of 205.5° C. to 208.5° C. at a scan rate of 10° C./minute; and/or 3) a dynamic moisture sorption (DMS) profile with an adsorption phase from 30% RH to 90% RH wherein the crystalline free-plate habit gains about 0.2% weight or less at 90% RH.

In some embodiments, the crystalline free-plate habit has:
1) a powder X-ray diffraction pattern comprising peaks, in terms of 2θ, at 8.2°±0.2°, 16.4°±0.2°, and 20.5°±0.2°;
2) a differential scanning calorimetry trace comprising an endotherm with an extrapolated onset temperature of 207.1° C. to 208.1° C. at a scan rate of 10° C./minute; and/or
3) a dynamic moisture sorption (DMS) profile with an adsorption phase from 30% RH to 90% RH wherein the crystalline free-plate habit gains about 0.2% weight or less at 90% RH.

In some embodiments, the crystalline free-plate habit has:
1) a differential scanning calorimetry trace comprising an endotherm with an extrapolated onset temperature of 205.0° C. to 208.5° C. at a scan rate of 10° C./minute; and/or
2) a dynamic moisture sorption (DMS) profile with an adsorption phase from 30% RH to 90% RH wherein the crystalline free-plate habit gains about 0.3% weight or less at 90% RH.

In some embodiments, the crystalline free-plate habit has:
1) a differential scanning calorimetry trace comprising an endotherm with an extrapolated onset temperature of 206.5° C. to t 208.5° C. at a scan rate of 10° C./minute; and/or
2) a dynamic moisture sorption (DMS) profile with an adsorption phase from 30% RH to 90% RH wherein the crystalline free-plate habit gains about 0.3% weight or less at 90% RH.

In some embodiments, the crystalline free-plate habit has:
1) a differential scanning calorimetry trace comprising an endotherm with an extrapolated onset temperature of 205.5° C. to 208.5° C. at a scan rate of 10° C./minute; and/or
2) a dynamic moisture sorption (DMS) profile with an adsorption phase from 30% RH to 90% RH wherein the crystalline free-plate habit gains about 0.2% weight or less at 90% RH.

In some embodiments, the crystalline free-plate habit has:
1) a differential scanning calorimetry trace comprising an endotherm with an extrapolated onset temperature of 207.1° C. to 208.1° C. at a scan rate of 10° C./minute; and/or
2) a dynamic moisture sorption (DMS) profile with an adsorption phase from 30% RH to 90% RH wherein the crystalline free-plate habit gains about 0.2% weight or less at 90% RH. In some embodiments, the crystalline free-plate habit has:
1) a powder X-ray diffraction pattern comprising peaks, in terms of 2θ, at 8.2°±0.2°, 16.4°±0.2°, and 20.5°±0.2°;
2) a differential scanning calorimetry trace comprising an endotherm with an extrapolated onset temperature of 205.0° C. to 208.5° C. at a scan rate of 10° C./minute;
3) a dynamic moisture sorption (DMS) profile with an adsorption phase from 30% RH to 90% RH wherein said crystalline free-plate habit gains about 0.3% weight or less at 90% RH; and/or
4) a BET specific surface area of about 0.1 m²/g to about 5.0 m²/g. In some embodiments, the crystalline free-plate habit has:
1) a powder X-ray diffraction pattern comprising peaks, in terms of 2θ, at 8.2°±0.2°, 20.5°±0.2°, and 24.6°±0.2°;
2) a differential scanning calorimetry trace comprising an endotherm with an extrapolated onset temperature of 205.5° C. to t 208.5° C. at a scan rate of 10° C./minute;
3) a dynamic moisture sorption (DMS) profile with an adsorption phase from 30% RH to 90% RH wherein said crystalline free-plate habit gains about 0.3% weight or less at 90% RH; and/or
4) a BET specific surface area of about 0.1 m²/g to about 4.0 m²/g.

In some embodiments, the crystalline free-plate habit has:
1) a powder X-ray diffraction pattern comprising peaks, in terms of 2θ, at 8.2°±0.2°, 20.5°±0.2°, and 24.6°±0.2°;
2) a differential scanning calorimetry trace comprising an endotherm with an extrapolated onset temperature of 205.5° C. to t 208.5° C. at a scan rate of 10° C./minute;
3) a dynamic moisture sorption (DMS) profile with an adsorption phase from 30% RH to 90% RH wherein said crystalline free-plate habit gains about 0.3% weight or less at 90% RH; and/or
4) a BET specific surface area of about 0.3 m²/g to about 3.0 m²/g.

In some embodiments, the crystalline free-plate habit has:
1) a powder X-ray diffraction pattern comprising peaks, in terms of 2θ, at 8.2°±0.2°, 16.4°±0.2°, 20.5°±0.2°, and 24.6°±0.2°;
2) a differential scanning calorimetry trace comprising an endotherm with an extrapolated onset temperature of 205.5° C. to 208.5° C. at a scan rate of 10° C./minute;
3) a dynamic moisture sorption (DMS) profile with an adsorption phase from 30% RH to 90% RH wherein said crystalline free-plate habit gains about 0.3% weight or less at 90% RH; and/or
4) a BET specific surface area of about 0.6 m²/g to about 4.0 m²/g.

In some embodiments, the crystalline free-plate habit has:
1) a powder X-ray diffraction pattern comprising peaks, in terms of 2°, at 8.2°±0.2°, 16.4°±0.2°, 20.5°±0.2°, and 24.6°±0.2°;
2) a differential scanning calorimetry trace comprising an endotherm with an extrapolated onset temperature of 206.5° C. to t 208.5° C. at a scan rate of 10° C./minute;
3) a dynamic moisture sorption (DMS) profile with an adsorption phase from 30% RH to 90% RH wherein said crystalline free-plate habit gains about 0.3% weight or less at 90% RH; and/or
4) a BET specific surface area of about 0.4 m²/g to about 2.0 m²/g.

In some embodiments, the crystalline free-plate habit has:
1) a powder X-ray diffraction pattern comprising peaks, in terms of 2θ, at 8.2°±0.2°, 16.4°±0.2°, 20.5°±0.2°, 24.6°±0.2°, and 28.8°±0.2°;
2) a differential scanning calorimetry trace comprising an endotherm with an extrapolated onset temperature of 206.5° C. to 208.1° C. at a scan rate of 10° C./minute;
3) a dynamic moisture sorption (DMS) profile with an adsorption phase from 30% RH to 90% RH wherein said crystalline free-plate habit gains about 0.2% weight or less at 90% RH; and/or
4) a BET specific surface area of about 0.5 m²/g to about 1.8 m²/g.

In some embodiments, the crystalline free-plate habit has:
1) a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°;
2) a differential scanning calorimetry trace comprising an endotherm with an extrapolated onset temperature of 205.5° C. to 208.1° C. at a scan rate of 10° C./minute;

3) a dynamic moisture sorption (DMS) profile with an adsorption phase from 30% RH to 90% RH wherein said crystalline free-plate habit gains about 0.2% weight or less at 90% RH; and/or
4) a BET specific surface area of about 0.6 m²/g to about 4.0 m²/g.

In some embodiments, the crystalline free-plate habit has:
1) a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°;
2) a differential scanning calorimetry trace comprising an endotherm with an extrapolated onset temperature of 207.1° C. to 208.1° C. at a scan rate of 10° C./minute;
3) a dynamic moisture sorption (DMS) profile with an adsorption phase from 30% RH to 90% RH wherein said crystalline free-plate habit gains about 0.2% weight or less at 90% RH; and/or
4) a BET specific surface area of about 0.6 m²/g to about 1.6 m²/g.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a powder X-ray diffraction pattern comprising peaks, in terms of 2θ, at 8.2°±0.2°, 16.4°±0.2°, and 20.5°±0.2°. In some embodiments, the crystalline free-plate habit has a powder X-ray diffraction pattern comprising peaks, in terms of 2θ, at 8.2°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, and 28.8°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a differential scanning calorimetry trace comprising an endotherm with an extrapolated onset temperature of 205.0° C. to 208.5° C. when scanned at 10° C. per minute. In some embodiments, the crystalline free-plate habit has a differential scanning calorimetry trace comprising an endotherm with an extrapolated onset temperature of 205.0° C. to 208.1° C. at a scan rate of 10° C./minute. In some embodiments, the crystalline free-plate habit has a differential scanning calorimetry trace comprising an endotherm with an extrapolated onset temperature of 205.5° C. to 208.5° C. at a scan rate of 10° C./minute. In some embodiments, the crystalline free-plate habit has a differential scanning calorimetry trace comprising an endotherm with an extrapolated onset temperature of 205.5° C. to 208.1° C. at a scan rate of 10° C./minute. In some embodiments, the crystalline free-plate habit has a differential scanning calorimetry trace comprising an endotherm with an extrapolated onset temperature of 206.0° C. to 208.5° C. at a scan rate of 10° C./minute. In some embodiments, the crystalline free-plate habit has a differential scanning calorimetry trace comprising an endotherm with an extrapolated onset temperature of 206.5° C. to 208.5° C. at a scan rate of 10° C./minute. In some embodiments, the crystalline free-plate habit has a differential scanning calorimetry trace comprising an endotherm with an extrapolated onset temperature of 206.5° C. to 208.1° C. at a scan rate of 10° C./minute. In some embodiments, the crystalline free-plate habit has a differential scanning calorimetry trace comprising an endotherm with an extrapolated onset temperature of 207.0° C. to 208.1° C. at a scan rate of 10° C./minute. In some embodiments, the crystalline free-plate habit has a powder X-ray diffraction pattern comprising peaks, in terms of 2θ, at 8.2°±0.2°, 16.4°±0.2°, and 20.5°±0.2°. In some embodiments, the crystalline free-plate habit has a powder X-ray diffraction pattern comprising peaks, in terms of 2θ, at 8.2°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, and 28.8°±0.2°. In some embodiments, the crystalline free plate habit has a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°.

One aspect of the present invention relates to a crystalline free-plate habit of L-arginine salt of (R)-2-(7-(4-cyclopentyl-3-(trifluoromethyl)benzyloxy)-1,2,3,4-tetrahydrocyclopenta[b]indol-3-yl)acetic acid having a BET specific surface area of about 0.1 m²/g to about 5.0 m²/g. In some embodiments, the crystalline free-plate habit has a BET specific surface area of about 0.1 m²/g to about 4.0 m²/g. In some embodiments, the crystalline free-plate habit has a BET specific surface area of about 0.3 m²/g to about 4.0 m²/g. In some embodiments, the crystalline free-plate habit has a BET specific surface area of about 0.5 m²/g to about 4.0 m²/g. In some embodiments, the crystalline free-plate habit has a BET specific surface area of about 0.6 m²/g to about 4.0 m²/g. In some embodiments, the crystalline free-plate habit has a BET specific surface area of about 0.3 m²/g to about 3.0 m²/g. In some embodiments, the crystalline free-plate habit has a BET specific surface area of about 0.4 m²/g to about 2.0 m²/g. In some embodiments, the crystalline free-plate habit has a BET specific surface area of about 0.5 m²/g to about 1.8 m²/g. In some embodiments, the crystalline free-plate habit has a BET specific surface area of about 0.6 m²/g to about 1.6 m²/g. In some embodiments, the crystalline free-plate habit has a powder X-ray diffraction pattern comprising peaks, in terms of 2θ, at 8.2°±0.2°, 16.4°±0.2°, and 20.5°±0.2°. In some embodiments, the crystalline free-plate habit has a powder X-ray diffraction pattern comprising peaks, in terms of 2θ, at 8.2°±0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°+0.2°, 20.5°±0.2°, and 24.6°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, and 28.8°±0.2°. In some embodiments, the crystalline free-plate habit has a powder X-ray diffraction pattern comprising peaks, in terms of 2θ, at 8.2°±0.2°, 16.4°±0.2°, 20.5°±0.2°, 24.6°±0.2°, 28.8°±0.2°, and 37.3°±0.2°.

CERTAIN EMBODIMENTS

In its various embodiments, the present invention is directed to, inter alia, methods of treating active skin extra-intestinal manifestations (EIM) in an inflammatory bowel disease (IBD) individual in need thereof comprising administering a therapeutically effective amount of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof.

In other embodiments, the present invention is directed to uses of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of active skin extra-intestinal manifestations (EIM) in an individual with inflammatory bowel disease (IBD).

In some embodiments, the individual has at least one condition selected from the group consisting of: psoriasis, erythema nodosum (EN), and pyoderma gangrenosum (PG).

In some embodiments, the individual has psoriasis.

In some embodiments, the individual has erythema nodosum (EN).

In some embodiments, the individual has pyoderma gangrenosum (PG).

In some embodiments, the skin extra-intestinal manifestations (EIM) is psoriasis.

In some embodiments, the skin extra-intestinal manifestations (EIM) is erythema nodosum (EN).

In some embodiments, the skin extra-intestinal manifestations (EIM) is pyoderma gangrenosum (PG).

In some embodiments, the skin extra-intestinal manifestations (EIM) is pyoderma gangrenosum (PG).

In some embodiments, the Compound 1, or a pharmaceutically acceptable salt, hydrate, or solvate thereof, is in an amount equivalent to about 1 mg to about 5 mg of Compound 1.

In some embodiments, the Compound 1, or a pharmaceutically acceptable salt, hydrate, or solvate thereof, is in an amount equivalent to about 1 mg to about 2 mg.

In some embodiments, the Compound 1, or a pharmaceutically acceptable salt, hydrate, or solvate thereof, is in an amount equivalent to about 1 mg or about 2 mg.

In some embodiments, the Compound 1, or a pharmaceutically acceptable salt, hydrate, or solvate thereof, is in an amount equivalent to about 1 mg of Compound 1.

In some embodiments, the Compound 1, or a pharmaceutically acceptable salt, hydrate, or solvate thereof, is in an amount equivalent to about 2 mg of Compound 1.

In some embodiments, the Compound 1, or a pharmaceutically acceptable salt, hydrate, or solvate thereof, is selected from: Compound 1, a calcium salt of Compound 1, and an L-arginine salt of Compound 1.

In some embodiments, the Compound 1, or a pharmaceutically acceptable salt, hydrate, or solvate thereof, is an L-arginine salt of Compound 1.

In some embodiments, the Compound 1, or a pharmaceutically acceptable salt, hydrate, or solvate thereof, is an anhydrous, non-solvated crystalline form of the L-arginine salt of Compound 1.

In some embodiments, the Compound 1, or a pharmaceutically acceptable salt, hydrate, or solvate thereof, is a crystalline free-plate habit of the non-solvated L-arginine salt of Compound 1.

In some embodiments, the Compound 1, or a pharmaceutically acceptable salt, hydrate, or solvate thereof, is an anhydrous, non-solvated crystalline form of Compound 1.

In some embodiments, the Compound 1, or a pharmaceutically acceptable salt, hydrate, or solvate thereof, is administered orally.

In some embodiments, the Compound 1, or a pharmaceutically acceptable salt, hydrate, or solvate thereof, is formulated as a capsule or tablet suitable for oral administration.

In some embodiments, the Compound 1, or a pharmaceutically acceptable salt, hydrate, or solvate thereof, is administered once daily.

In some embodiments, the Compound 1, or a pharmaceutically acceptable salt, hydrate, or solvate thereof, is administered without food.

In some embodiments, the methods further comprise administering Compound 1, or a pharmaceutically salt, solvate, or hydrate thereof, in combination with a therapeutically effective amount of a compound selected from the group consisting of: a corticosteroid, a 5-aminosalicylic acid derivative, and a TNF-alpha inhibitor.

In some embodiments, Compound 1 or a pharmaceutically salt, solvate, or hydrate thereof is administered to an individual who is also being administered a therapeutically effective amount of a compound selected from the group consisting of: a corticosteroid, a 5-aminosalicylic acid derivative, and a TNF-alpha inhibitor.

In some embodiments, when administered with Compound 1, an individual is administered a reduced amount of the compound selected from the group consisting of: a corticosteroid, a 5-aminosalicylic acid derivative, and a TNF-alpha inhibitor.

In some embodiments, the corticosteroid is cortisone, dexamethasone, hydrocortisone, methylprednisolone, prednisolone, prednisone, triamcinolone, and fludrocortisone.

In some embodiments, the 5-aminosalicylic acid derivative is selected from the group consisting of: balsalazide, mesalamine, olsalazine, and sulfasalazine.

In some embodiments, the TNF-alpha inhibitor is selected from the group consisting of: as infliximab (Remicade®), adalimumab (Humira®), certolizumab pegol (Cimzia®), and golimumab (Simponi®), and etanercept (Enbrel®).

In still other embodiments, the present invention is directed to, inter alia, methods of treating pyoderma gangrenosum (PG) in an individual in need thereof comprising administering a therapeutically effective amount of (R)-2-(7-(4-cyclopentyl-3-(trifluoromethyl)benzyloxy)-1,2,3,4- tetrahydrocyclopenta[b]indol-3-yl)acetic acid (Compound 1), or a pharmaceutically acceptable salt, hydrate, or solvate thereof.

In some embodiments, the individual has at least one condition selected from the group consisting of: an inflammatory bowel disease, arthritis, a hematological disease, and an autoinflammatory disease.

In some embodiments, the individual has at least one condition selected from the group consisting of: ulcerative colitis and Crohn's disease.

In some embodiments, the individual has at least one condition selected from the group consisting of: rheumatoid arthritis and seronegative arthritis.

In some embodiments, the individual has at least one condition selected from the group consisting of: myelocytic leukemia, hairy cell leukemia, myelofibrosis, myeloid metaplasia, and monoclonal gammopathy.

In some embodiments, the individual has at least one condition selected from the group consisting of: PAPA syndrome and granulomatosis with polyangiitis.

In some embodiments, the Compound 1, or a pharmaceutically acceptable salt, hydrate, or solvate thereof, is in an amount equivalent to about 1 mg to about 5 mg of Compound 1.

In some embodiments, the Compound 1, or a pharmaceutically acceptable salt, hydrate, or solvate thereof, is in an amount equivalent to about 1 mg to about 2 mg.

In some embodiments, the Compound 1, or a pharmaceutically acceptable salt, hydrate, or solvate thereof, is in an amount equivalent to about 1 mg or about 2 mg.

In some embodiments, the Compound 1, or a pharmaceutically acceptable salt, hydrate, or solvate thereof, is in an amount equivalent to about 1 mg of Compound 1.

In some embodiments, the Compound 1, or a pharmaceutically acceptable salt, hydrate, or solvate thereof, is in an amount equivalent to about 2 mg of Compound 1.

In some embodiments, the Compound 1, or a pharmaceutically acceptable salt, hydrate, or solvate thereof, is selected from: Compound 1, a calcium salt of Compound 1, and an L-arginine salt of Compound 1.

In some embodiments, the Compound 1, or a pharmaceutically acceptable salt, hydrate, or solvate thereof, is an L-arginine salt of Compound 1.

In some embodiments, the Compound 1, or a pharmaceutically acceptable salt, hydrate, or solvate thereof, is an anhydrous, non-solvated crystalline form of the L-arginine salt of Compound 1.

In some embodiments, the Compound 1, or a pharmaceutically acceptable salt, hydrate, or solvate thereof, is a crystalline free-plate habit of the non-solvated L-arginine salt of Compound 1.

In some embodiments, the Compound 1, or a pharmaceutically acceptable salt, hydrate, or solvate thereof, is an anhydrous, non-solvated crystalline form of Compound 1.

In some embodiments, the Compound 1, or a pharmaceutically acceptable salt, hydrate, or solvate thereof, is administered orally.

In some embodiments, the Compound 1, or a pharmaceutically acceptable salt, hydrate, or solvate thereof, is formulated as a capsule or tablet suitable for oral administration.

In some embodiments, the methods further comprise administering Compound 1, or a pharmaceutically salt, solvate, or hydrate thereof, in combination with a therapeutically effective amount of a compound selected from the group consisting of: a corticosteroid, an immunosuppressant, a biologic, an anti-inflammatory agent, and an antibiotic.

In some embodiments, the corticosteroid is cortisone, dexamethasone, hydrocortisone, methylprednisolone, prednisolone, prednisone, triamcinolone, and fludrocortisone.

In some embodiments, the immunosuppressant is selected from the group consisting of: cyclosporin A, tacrolimus, and mycophenolic acid.

In some embodiments, the immunosuppressant is cyclosporin A.

In some embodiments, the biologic is selected from the group consisting of: abatacept, adalimumab, adalimumab-atto, anakinra, certolizumab pegol, etanercept, etanercept-szzs, golimumab, infliximab, infliximab-dyyb, rituximab, tocilizumab, tofacitinib, vedolizumab, and natalizumab. Additional names, such as their marketed names for the biologics include: abatacept (Orencia®), adalimumab (Humira®), adalimumab-atto (Amjevita®) a biosimilar to Humira, anakinra (Kineret®), certolizumab pegol (Cimzia®), etanercept (Enbrel®, etanercept-szzs (Erelzi®) a biosimilar to Enbrel, golimumab (Simponi®, Simponi Aria®), infliximab (Remicade®), infliximab-dyyb (Inflectra®) a biosimilar to Remicade, rituximab (Rituxan®), tocilizumab (Actemra®), tofacitinib (Xeljanz®), vedolizumab (Entyvio®), and natalizumab (Tysabri®).

In some embodiments, the anti-inflammatory agent is selected from the group consisting of: aceclofenac, vedolizumab, aspirin, celecoxib, clonixin, dexibuprofen, dexketoprofen, diclofenac, diflunisal, droxicam, enolic acid, etodolac, etoricoxib, fenoprofen, flufenamic acid, flurbiprofen, ibuprofen, indomethacin, ketoprofen, ketorolac, licofelone, lornoxicam, loxoprofen, meclofenamic acid, mefenamic acid, meloxicam, nabumetone, naproxen, oxaprozin, parecoxib, phenylbutazone, piroxicam, salicylic acid, salsalate, sulindac, tenoxicam, tolfenamic acid, and tolmetin.

In some embodiments, the antibiotic is selected from the group consisting of: ceftobiprole, ceftaroline, clindamycin, dalbavancin, daptomycin, fusidic acid, linezolid, mupirocin, oritavancin, tedizolid, telavancin, tigecycline, vancomycin, amikacin, gentamicin, kanamycin, neomycin, netilmicin, tobramycin, and paromomycin.

In some embodiments, the antibiotic is selected from the group consisting of: mupirocin and gentamicin.

In other embodiments, the present invention is directed to uses of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in the manufacture of a medicament for the treatment of pyoderma gangrenosum (PG) in an individual.

In some embodiments, the individual has at least one condition selected from the group consisting of: an inflammatory bowel disease, arthritis, a hematological disease, and an autoinflammatory disease.

In some embodiments, the individual has at least one condition selected from the group consisting of: ulcerative colitis and Crohn's disease.

In some embodiments, the individual has at least one condition selected from the group consisting of: rheumatoid arthritis and seronegative arthritis.

In some embodiments, the individual has at least one condition selected from the group consisting of: myelocytic leukemia, hairy cell leukemia, myelofibrosis, myeloid metaplasia, and monoclonal gammopathy.

In some embodiments, the individual has at least one condition selected from the group consisting of: PAPA syndrome and granulomatosis with polyangiitis.

In some embodiments, the Compound 1, or a pharmaceutically acceptable salt, hydrate, or solvate thereof, is in an amount equivalent to about 1 mg to about 5 mg of Compound 1.

In some embodiments, the Compound 1, or a pharmaceutically acceptable salt, hydrate, or solvate thereof, is in an amount equivalent to about 2 mg of Compound 1.

In some embodiments, the Compound 1, or a pharmaceutically acceptable salt, hydrate, or solvate thereof, is selected from: Compound 1, a calcium salt of Compound 1, and an L-arginine salt of Compound 1.

In some embodiments, the Compound 1, or a pharmaceutically acceptable salt, hydrate, or solvate thereof, is an L-arginine salt of Compound 1.

In some embodiments, the Compound 1, or a pharmaceutically acceptable salt, hydrate, or solvate thereof, is an anhydrous, non-solvated crystalline form of the L-arginine salt of Compound 1.

In some embodiments, the Compound 1, or a pharmaceutically acceptable salt, hydrate, or solvate thereof, is a crystalline free-plate habit of the non-solvated L-arginine salt of Compound 1.

In some embodiments, the Compound 1, or a pharmaceutically acceptable salt, hydrate, or solvate thereof, is an anhydrous, non-solvated crystalline form of Compound 1.

In some embodiments, the Compound 1, or a pharmaceutically acceptable salt, hydrate, or solvate thereof, is administered orally.

In some embodiments, the Compound 1, or a pharmaceutically acceptable salt, hydrate, or solvate thereof, is formulated as a capsule or tablet suitable for oral administration.

In some embodiments, the Compound 1, or a pharmaceutically acceptable salt, hydrate, or solvate thereof, is administered once daily.

In some embodiments, the Compound 1, or a pharmaceutically acceptable salt, hydrate, or solvate thereof, is administered without food.

In some embodiments, the methods further comprise administering Compound 1, or a pharmaceutically salt, solvate, or hydrate thereof, in combination with a therapeutically effective amount of a compound selected from the group consisting of: a corticosteroid, an immunosuppressant, a biologic, an anti-inflammatory agent, and an antibiotic.

In some embodiments, the corticosteroid is cortisone, dexamethasone, hydrocortisone, methylprednisolone, prednisolone, prednisone, triamcinolone, and fludrocortisone.

In some embodiments, the immunosuppressant is selected from the group consisting of: cyclosporin A, tacrolimus, and mycophenolic acid.

In some embodiments, the immunosuppressant is cyclosporin A.

In some embodiments, the biologic is selected from the group consisting of: abatacept, adalimumab, adalimumab-atto, anakinra, certolizumab pegol, etanercept, etanercept-szzs, golimumab, infliximab, infliximab-dyyb, rituximab, tocilizumab, tofacitinib, vedolizumab, and natalizumab. Additional names, such as their marketed names for the biologics include: abatacept (Orencia®), adalimumab (Humira®), adalimumab-atto (Amjevita®) a biosimilar to Humira, anakinra (Kineret®), certolizumab pegol (Cimzia®), etanercept (Enbrel®, etanercept-szzs (Erelzi®) a biosimilar to Enbrel, golimumab (Simponi®, Simponi Aria®), infliximab (Remicade®), infliximab-dyyb (Inflectra®) a biosimilar to Remicade, rituximab (Rituxan®), tocilizumab (Actemra®), tofacitinib (Xeljanz®), vedolizumab (Entyvio®), and natalizumab (Tysabri®).

In some embodiments, the anti-inflammatory agent is selected from the group consisting of: aceclofenac, vedolizumab, aspirin, celecoxib, clonixin, dexibuprofen, dexketoprofen, diclofenac, diflunisal, droxicam, enolic acid, etodolac, etoricoxib, fenoprofen, flufenamic acid, flurbiprofen, ibuprofen, indomethacin, ketoprofen, ketorolac, licofelone, lornoxicam, loxoprofen, meclofenamic acid, mefenamic acid, meloxicam, nabumetone, naproxen, oxaprozin, parecoxib, phenylbutazone, piroxicam, salicylic acid, salsalate, sulindac, tenoxicam, tolfenamic acid, and tolmetin.

In some embodiments, the antibiotic is selected from the group consisting of: ceftobiprole, ceftaroline, clindamycin, dalbavancin, daptomycin, fusidic acid, linezolid, mupirocin, oritavancin, tedizolid, telavancin, tigecycline, vancomycin, amikacin, gentamicin, kanamycin, neomycin, netilmicin, tobramycin, and paromomycin.

In some embodiments, the antibiotic is selected from the group consisting of: mupirocin and gentamicin.

In some embodiments, the pyoderma gangrenosum is classic pyoderma gangrenosum.

In some embodiments, the individual is experiencing an inflammatory episode of pyoderma gangrenosum.

In some embodiments, the individual has at least one ulcer located on their leg.

In some embodiments, the individual has at least one ulcer located on their hand.

In some embodiments, the pyoderma gangrenosum is selected from at least one of the following: peristomal pyoderma gangrenosum, bullous pyoderma gangrenosum, pustular pyoderma gangrenosum, and vegetative pyoderma gangrenosum.

In some embodiments, the individual has at least one active pyoderma gangrenosum ulcer.

In some embodiments, the individual has at least one active, non-healing pyoderma gangrenosum ulcer.

In some embodiments, the individual does not have inflammatory bowel disease.

In some embodiments, the individual does not have ulcerative colitis.

In some embodiments, the individual does not have Crohn's disease.

In some embodiments, Compound 1 is administered without food.

In some embodiments, the individual is administered the therapeutically effective amount of Compound 1 once daily.

Pharmaceutical Compositions

A further aspect of the present invention pertains to pharmaceutical compositions comprising one or more compounds as described herein and one or more pharmaceutically acceptable carriers. Some embodiments pertain to pharmaceutical compositions comprising a compound of the present invention and a pharmaceutically acceptable carrier.

Some embodiments of the present invention include a method of producing a pharmaceutical composition comprising admixing at least one compound according to any of the compound embodiments disclosed herein and a pharmaceutically acceptable carrier.

Formulations may be prepared by any suitable method, typically by uniformly mixing the active compound(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the compound of the invention in a suitable liquid vehicle and filter sterilizing the solution before filling and sealing an appropriate vial or ampule. These are just a few examples of the many appropriate methods well known in the art for preparing dosage forms.

A compound of the present invention can be formulated into pharmaceutical compositions using techniques well known to those in the art. Suitable pharmaceutically acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.) While it is possible that, for use in the prophylaxis or treatment, a compound of the invention may, in an alternative use, be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt, solvate, hydrate or derivative thereof together with one or more pharmaceutically acceptable carriers thereof and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation, insufflation or by a transdermal patch. Transdermal patches dispense a drug at a controlled rate by presenting the drug for absorption in an efficient manner with a minimum of degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The compounds of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use; in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or suspensions, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Compounds of the present invention or a salt, solvate, hydrate or physiologically functional derivative thereof can be used as active ingredients in pharmaceutical compositions, specifically as S1P1 receptor modulators. The term "active ingredient" is defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the compounds of the present invention can vary and as is customary and known to the physician, it is to be tailored to the individual conditions in each individual case. It depends, for example, on the nature and severity of the illness to be treated, on the condition of the individual, on the compound employed or on whether an acute or chronic disease state is treated or prophylaxis is conducted or on whether further active compounds are administered in addition to the compounds of the present invention. Representative doses of the present invention include, but are not limited to, about 1 mg to about 5 mg, about 1 mg, about 1.25 mg, about 1.5 mg, about 1.75 mg, about 2 mg, about 2.25 mg, about 2.5 mg, about 2.75 mg, about 3 mg, about 3.25 mg, about 3.5 mg, about 3.75 mg, about 4 mg, about 4.25 mg, about 4.5 mg, about 4.75 mg, and about 5 mg. Multiple doses may be administered during the day, especially when relatively large amounts are deemed to be needed, for example 2, 3 or 4 doses. Depending on the individual and as deemed appropriate by the individual's physician or caregiver it may be necessary to deviate upward or downward from the doses described herein.

The amount of active ingredient or an active salt, solvate or hydrate derivative thereof, required for use in treatment will vary not only with the particular salt selected but also with the route of administration, the nature of the condition being treated and the age and condition of the individual and will ultimately be at the discretion of the attendant physician or clinician. Representative factors include the type, age, weight, sex, diet and medical condition of the individual, the severity of the disease, the route of administration, pharmacological considerations such as the activity, efficacy, pharmacokinetic and toxicology profiles of the particular compound employed, whether a drug delivery system is utilized, whether an acute or chronic disease state is being treated or prophylaxis is conducted or whether further active compounds are administered in addition to the compounds of the present invention and as part of a drug combination. The dosage regimen for treating a disease condition with the compounds and/or compositions of this invention is selected in accordance with a variety factors including those cited above. Thus, the actual dosage regimen employed may vary widely and therefore may deviate from a preferred dosage regimen and one skilled in the art will recognize that dosage and dosage regimens outside these typical ranges can be tested and, where appropriate, may be used in the methods of this invention.

The desired dose may conveniently be presented in a single dose or as divided doses administered at appropriate intervals, for example, as 2, 3, 4 or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

For preparing pharmaceutical compositions from the compounds of the present invention, the suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or encapsulating materials.

In powders, the carrier is a finely divided solid which is in a mixture with the finely divided active component.

In tablets, the active component is mixed with the carrier having the necessary binding capacity in suitable proportions and compacted to the desired shape and size.

The powders and tablets may contain varying percentage amounts of the active compound. A representative amount in a powder or tablet may be from 0.5 to about 90 percent of the active compound. However, an artisan would know when amounts outside of this range are necessary. Suitable carriers for powders and tablets include magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein (e.g., by stirring). The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising the active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the individual administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the present invention or pharmaceutical compositions comprising them are administered as aerosols (e.g., nasal aerosols, by inhalation), this can be carried out, for example, using a spray, a nebulizer, a pump nebulizer, an inhalation apparatus, a metered inhaler or a dry powder inhaler. Pharmaceutical forms for administration of the compounds of the present invention as an aerosol can be prepared by processes well known to the person skilled in the art. Solutions or dispersions of the compounds of the present invention or a pharmaceutically acceptable salt, solvate, hydrate or derivative thereof in water, water/alcohol mixtures or suitable saline solutions, for example, can be employed using customary additives (e.g., benzyl alcohol or other suitable preservatives), absorption enhancers for increasing the bioavailability, solubilizers, dispersants and others and, if appropriate, customary propellants (e.g., carbon dioxide, CFCs, such as, dichlorodifluoromethane, trichlorofluoromethane, dichlorotetrafluoroethane and the like). The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively, the active ingredients may be provided in the form of a dry powder (e.g., a powder mix of the compound in a suitable powder base such as lactose, starch, starch derivatives such as hydroxypropylmethyl cellulose and polyvinylpyrrolidone (PVP)). Conveniently the powder carrier will form a gel in the nasal cavity. The powder composition may be presented in unit dose form (e.g., capsules, cartridges) as for gelatin or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

In some embodiments, the compositions are tablets or capsules for oral administration.

In some embodiments, the compositions are liquids for intravenous administration.

The compounds according to the invention may optionally exist as pharmaceutically acceptable salts including pharmaceutically acceptable acid addition salts prepared from pharmaceutically acceptable non-toxic acids including inorganic and organic acids. Representative acids include, but are not limited to, acetic, benzenesulfonic, benzoic, camphorsulfonic, citric, ethenesulfonic, dichloroacetic, formic, fumaric, gluconic, glutamic, hippuric, hydrobromic, hydrochloric, isethionic, lactic, maleic, malic, mandelic, methanesulfonic, mucic, nitric, oxalic, pamoic, pantothenic, phosphoric, succinic, sulfiric, tartaric, oxalic, p-toluenesulfonic and the like, such as those pharmaceutically acceptable salts listed by Berge et al., *Journal of Pharmaceutical Sciences*, 66:1-19 (1977), incorporated herein by reference in its entirety.

The acid addition salts may be obtained as the direct products of compound synthesis. In the alternative, the free base may be dissolved in a suitable solvent containing the appropriate acid and the salt isolated by evaporating the solvent or otherwise separating the salt and solvent. The compounds of this invention may form solvates with standard low molecular weight solvents using methods known to the skilled artisan.

Compounds of the present invention can be converted to "pro-drugs." The term "pro-drugs" refers to compounds that have been modified with specific chemical groups known in the art and that when administered into an individual undergo biotransformation to give the parent compound. Pro-drugs can thus be viewed as compounds of the invention containing one or more specialized non-toxic protective groups used in a transient manner to alter or to eliminate a property of the compound. In one general aspect, the "pro-drug" approach is utilized to facilitate oral absorption. A thorough discussion is provided in T. Higuchi and V. Stella, Pro-drugs as Novel Delivery Systems Vol. 14 of the A.C.S. Symposium Series; and in *Bioreversible Carriers in Drug Design*, ed. Edward B. Roche, American Pharmaceutical Association and Pergamon Press, 1987, both of which are hereby incorporated by reference in their entirety.

Some embodiments of the present invention include a method of producing a pharmaceutical composition for "combination-therapy" comprising admixing at least one compound according to any of the compound embodiments disclosed herein, together with at least one known pharmaceutical agent as described herein and a pharmaceutically acceptable carrier.

As will be recognized, the steps of the methods of the present invention need not be performed any particular number of times or in any particular sequence. Additional objects, advantages and novel features of this invention will become apparent to those skilled in the art upon examination of the following examples thereof, which are intended to be illustrative and not intended to be limiting.

EXAMPLES

Example 1: Preparation of Compounds

The preparation of Compound 1, including certain crystal forms of Compound 1 are described in International Patent Application No. PCT/US2009/004265, published as International Publication No. WO2010/011316, and International Patent Application No. PCT/US2011/000153, published as International Publication No. WO2011/094008, the entire contents of each are incorporated herein by reference in their entirety.

The preparation of the crystalline free-plate habit of the non-solvated L-arginine salt of Compound 1 is described in International Patent Application No. PCT/US2016/038506, published as International Publication No. WO2016/209809, the entire contents of which are incorporated herein by reference in their entirety.

Example 2: Clinical Trial for Skin Extra-Intestinal Manifestation (EIM) with Compound 1

A clinical trial is conducted in 10-20 individuals with IBD and active skin extra-intestinal manifestations.

All visits in the study are ambulatory visits. A screening period of up to four weeks is followed by a 12-week treatment period. During the treatment period, individuals take one 2 mg tablet of Compound 1 once per day. The last dose is taken one day before the last treatment visit at week 12. A follow-up visit takes place two weeks after the end of treatment (FIG. 1).

Screening Visit:

Individuals visit the study site for screening assessments up to four weeks prior to the planned start of treatment.

Individuals start the 24-hour ambulatory pre-dose Holter (ECG) monitoring procedure at D-1.

Treatment Visits:

Visit (week 0, day 1):

Individuals return to the study site to receive the first dose of Compound 1 and remain at the study site for six hours for safety evaluation. Holter monitoring continues for another 18 hours.

Visits at week 1, week 2, week 4, week 8, and week 12:

Individuals return to the study site and undergo examinations at weeks 1, 2, 4, 8, and 12. The last dose of Compound 1 is administered one day before the last treatment visit at week 12.

Follow Up Visits/End of Study Visit:

Week 14 (Two Weeks after End of Treatment):

Individuals return to the study site for the final visit.

Premature Discontinuation:

Procedures planned for week 14 are performed for all individuals that discontinue the study prematurely.

Inclusion Criteria

1. Men or women of age 18 to 80 years, inclusive.
2. Able to give signed informed consent and willing and able to comply with the study requirements.
3. Considered to be in stable health in the opinion of the investigator as determined by:
   a.) A pre-study physical examination with no clinically significant abnormalities unrelated to IBD.
   b.) Vital signs (VS) at screening: pulse rate ≥55 bpm, systolic blood pressure (SBP) ≥90, and diastolic blood pressure (DBP) ≥55 mmHg.
   c.) Liver function tests (ALT/AST, bilirubin and alkaline phosphatase)<2× the upper limit of normal [ULN].
   d.) All other pre-study clinical laboratory findings within normal range, or if outside of the normal range not deemed clinically significant in the opinion of the investigator.
   e.) 12-lead electrocardiogram (ECG) showing no clinically significant abnormalities in the opinion of the investigator.
   f.) A chest x-ray showing no evidence of active pulmonary disease (a chest x-ray taken within the previous 12 months from the screening visit may also be used).
   g.) Ophthalmology evaluation (by an ophthalmologist) without evidence of macular edema, supported with OCT where available (dependent on site capability) no later than three months prior to screening.
4. Individuals receiving stable treatment for IBD and ELM.
5. Diagnosis of active psoriasis, erythema nodosum or pyoderma gangrenosum by physician assessments.
6. Diagnosis of ulcerative colitis (UC) or Crohn's disease (CD) established prior to screening by clinical and endoscopic evidence.

Permitted Medications for the Treatment of IBD (UC and CD)

Oral 5-ASA treatment is permitted for the treatment of IBD, provided that the individual is receiving the medication(s) at baseline, and that the dose(s) has been stable. These medications are to remain stable throughout the study.

Oral corticosteroids that the individual is receiving at baseline are continued, provided that the dose has been stable for two weeks prior to baseline. These medications are to remain stable at least eight weeks.

TNF-alpha inhibitor treatment is permitted provided that the dose remains stable throughout the study.

Probiotics (e.g., Culturelle, *Saccharomyces boulardii*) are permitted provided that the dose has been stable for the two weeks immediately prior to randomization.

Antidiarrheals are allowed throughout the study as necessary for control of chronic diarrhea.

Azathioprine or 6-mercaptopurine are permitted, provided that the dose has been stable for the eight weeks immediately prior to screening (these immunosuppressive agents are discontinued at the time of randomization).

Dermatological medications that the individual is receiving at baseline are continued, provided that these are stable for two weeks prior to baseline and remain stable throughout the study.

Physician's Global Assessment (PGA)

1) Disease Activity Score for CD

Patient reported outcomes (liquid stools, abdominal pain and general wellbeing) are captured in a daily diary by the individual. Patient reported outcomes can be reviewed by site personnel during screening and (prior to dosing, if applicable) at weeks 0, 1, 2, 4, 8 and 12 and at any unscheduled visit(s) due to disease exacerbation. Presence of extra-intestinal manifestation (arthritis/anthralgia, iritis/uveitis, skin/mouth lesion, peri-anal disease, other fistula, fever >37.8° C.), use of anti-diarrheals, abdominal mass, haematocrit and weight are captured weekly or at each visit. The investigator or designee calculates the disease activity scores taking into consideration the above data and the individual reported outcomes.

2) Physician Global Assessments for Active Skin Extra-Intestinal Manifestations

The Physician Global Assessment (PGA) is used as an instrument to measure skin disease activity (e.g., for EG, EN or psoriasis).

Patients Global Assessment for active skin extra-intestinal manifestations.

The Patients Global Assessment will be used to measure how individuals rate the severity and pain of their skin disease.

3) Dermatology Life Quality Index (DLQI)

This questionnaire measures how much of the individual's life is affected by their skin problems.

4) Psoriasis Area and Severity Index (PASI)

The PASI is a tool for the measurement of severity of psoriasis. PASI combines the assessment of the severity of lesions and the area affected into a single score in the range 0 (no disease) to 72 (maximum disease).

5) Inflammatory Bowel Disease Questionnaire (IBDQ)

The IBDQ is used to measure how the individual has felt during the last two weeks. The IBDQ is used during screening and at weeks 2, 4, 8, and 12.

6) Skin Punch Biopsies

Skin punch biopsies (from healthy skin and from target lesion) are collected before treatment and at week 8 or 12. Immunohistochemistry and other analysis methods (such as RT-PCR) are performed to evaluate immune cell infiltration, cytokine expression in the skin and other inflammatory parameters.

7) C-reactive Protein (CRP)

Blood samples for analysis of C-reactive protein (CRP) are collected at screening; at weeks 0, 1, 2, 4, 8, and 12; and at the two-week follow-up.

Efficacy Endpoints
- UC endpoint: Change from baseline in stool frequency, rectal bleeding, PGA (Physicians Global Assessments) at weeks 1, 2, 4, 8 and 12.
- CD endpoint: Change from baseline in disease activity score at week 1, 2, 4, 8 and 12.
- Change from baseline in endoscopic improvement/histologic healing using endoscopy or flexible proctosigmoidoscopy (only if there are signs of inflammation at screening another evaluation is performed at week 12).
- Change from baseline in level of fecal calprotectin at week 4, 8 and 12. Change from baseline in Physician Global Assessments for active skin extra-intestinal manifestations (PG, EN and psoriasis) at week 1, 2, 4, 8 and 12.
- Change from baseline in Patients Global Assessments for active skin extra-intestinal manifestations (PG, EN and psoriasis) at week 1, 2, 4, 8 and 12.
- Change from baseline in the Dermatology Life Quality Index (DLQI) score at week 1, 2, 4, 8 and 12.
- Psoriasis endpoint only (all other endpoints are for all skin manifestations): Change from baseline in Psoriasis Area and Severity Index (PASI) score at week 1, 2, 4, 8 and 12.
- Change from baseline in Inflammatory Bowel Disease Questionnaire (IBDQ) score at week 2, 4, 8 and 12.
- Skin punch biopsies (from healthy skin and from target lesion) are collected before treatment and at week 8 or 12. Immunohistochemistry and other analyzing methods such as RT-PCR are performed to evaluate immune cell infiltration, cytokine expression in the skin and other inflammatory parameters.
- Change from baseline in C-reactive protein (CRP) at weeks 1, 2, 4, 8 and 12.
- Change from baseline in leucocyte characterization.
- Change from baseline in lymphocyte counts at weeks 1, 2, 4, 8 and 12.

Example 3: Clinical Trial for Pyoderma Gangrenosum with Compound 1

A clinical trial is conducted in individuals aged 18 to 80 years old (inclusive) who have active pyoderma gangrenosum (PG) ulcers. All visits in the study are ambulatory visits. The screening period lasts up to four weeks and is followed by a 12-week treatment period. During the treatment period, individuals take one 2 mg tablet of Compound 1 once per day. The last dose is taken one day before the end of the treatment period (week 12). A follow-up visit takes place two weeks after the end of treatment.

Screening Visit

Each individual visits the study site for screening assessment within 4 weeks of the planned start of the treatment (Day 1). Individuals then undergo screening procedures to determine eligibility.

Individuals return to the study site at Day-1 for confirmation of eligibility, and start the 24-hour ambulatory pre-dose Holter (ECG) monitoring procedure.

Treatment Visits

Baseline Visit (Day 1): Individuals return to the study site to receive the first dose of Compound 1. Individuals are instructed to take the tablet first thing in the morning on an empty stomach. Individuals are advised not to crush, break, chew, or dissolve the tablet and to take study medication with an adequate amount of water. The individuals remain at the study site for at least six hours for safety evaluation. Holter monitoring continues to allow for an overall continuous 24-hour pre- and a 24-hour post-dose monitoring.

Visits at week 2, week 4, week 8, and week 12: Individuals return to the study site and tests are conducted. The last dose of Compound 1 is planned 1 day before the end of the treatment visit at week 12.

Follow Up Visit/End of Study Visit

Visit at week 14 (two weeks after end of treatment): Individuals return to the study site for the final visit.

Permitted Medications
- Oral corticosteroids
- TNF-alpha inhibitor (etanercept, infliximab, adalimumab or other)
- Oral 5-ASA medication
- Antidiarrheal treatment
- OTC analgesics (paracetamol/acetaminophen, NSAIDs)

Efficacy Endpoints
- Change from baseline (Day 1 pre-dose) to week 12 in Physician Global Assessments for active skin manifestations. Assessment of target lesion/ulceration:
  - 0: Total resolution of target ulcer with no signs of active PG
  - 1: Almost completely healed target ulcer with only minimal signs of active PG
  - 2: Evidence of target ulcer healing which involves at least 50% of ulcer/ulcer margin
  - 3: Evidence of target ulcer healing which involves less than 50% of ulcer/ulcer margin
  - 4: No evidence of target ulcer healing
- Change from baseline (Day 1 pre-dose) to week 12 in Patient Global Assessments for active skin manifestations: visual analog scale (VAS) for assessment of severity of the disease and severity of pain by patient.
- Change from baseline (Day 1 pre-dose) to week 12 in Dermatology Life Quality Index (DLQI).
- Change from baseline (Day 1 pre-dose) to week 12 in CRP levels.

The following measures are also assessed:
- Imaging (digital photos) of the target lesion.
- Evaluation of the changes in surface area of target lesion.
- Punch biopsy (histology).

Example 4: BET (Brunauer, Emmett, and Teller) Specific Surface Area Method (Plate Habit)

In general, the specific surface areas for crystalline free-plate habit of the non-solvated L-arginine salt of Compound 1 were determined by physical adsorption of nitrogen gas on the surface of the sample from each lot using the well-established technique based on the Brunauer, Emmett, and Teller theory.

The BET surface areas for the samples were measured by Micromeritics Pharmaceutical Services using a Micromeritics™ TriStar II BET surface area analyzer (MicroActive for TriStar II Plus 2.02 Software™). The samples were degassed at 25° C. for 960 minutes under vacuum (i.e., 100 mm/Hg). The determination of the adsorption of $N_2$ at 77.3 K was measured using a BET surface area eleven-point method with relative pressures in the range of about 0.05 to about 0.3 ($P/P_0$) for a weighed amount of each sample, see Table 1 below. The analysis was performed per ISO9277.

TABLE 1

| Arena Lot | Lot Number | Sample (g) | Correlation Coefficient | BET Surface Area (m$^2$/g) |
|---|---|---|---|---|
| 5015-12-12 | A1 | 0.6163 | 0.99916 | 0.7 |
| 5015-12-13 | A2 | 1.5270 | 0.99945 | 0.7 |
| 5015-12-14 | A3 | 0.4465 | 0.99922 | 1.5 |
| 5015-12-15 | A4 | 0.5709 | 0.99939 | 1.0 |
| 5015-12-16 | A5 | 0.9582 | 0.99940 | 0.8 |
| 04GSp | A6 | 0.4332 | 0.99921 | 2.4 |
| 05GSp | A7 | 0.3652 | 0.99910 | 1.9 |
| 06GSp | A8 | 0.6866 | 0.99984 | 3.0 |
| 07GSp | A9 | 0.2754 | 0.99914 | 3.1 |

Figure 4:
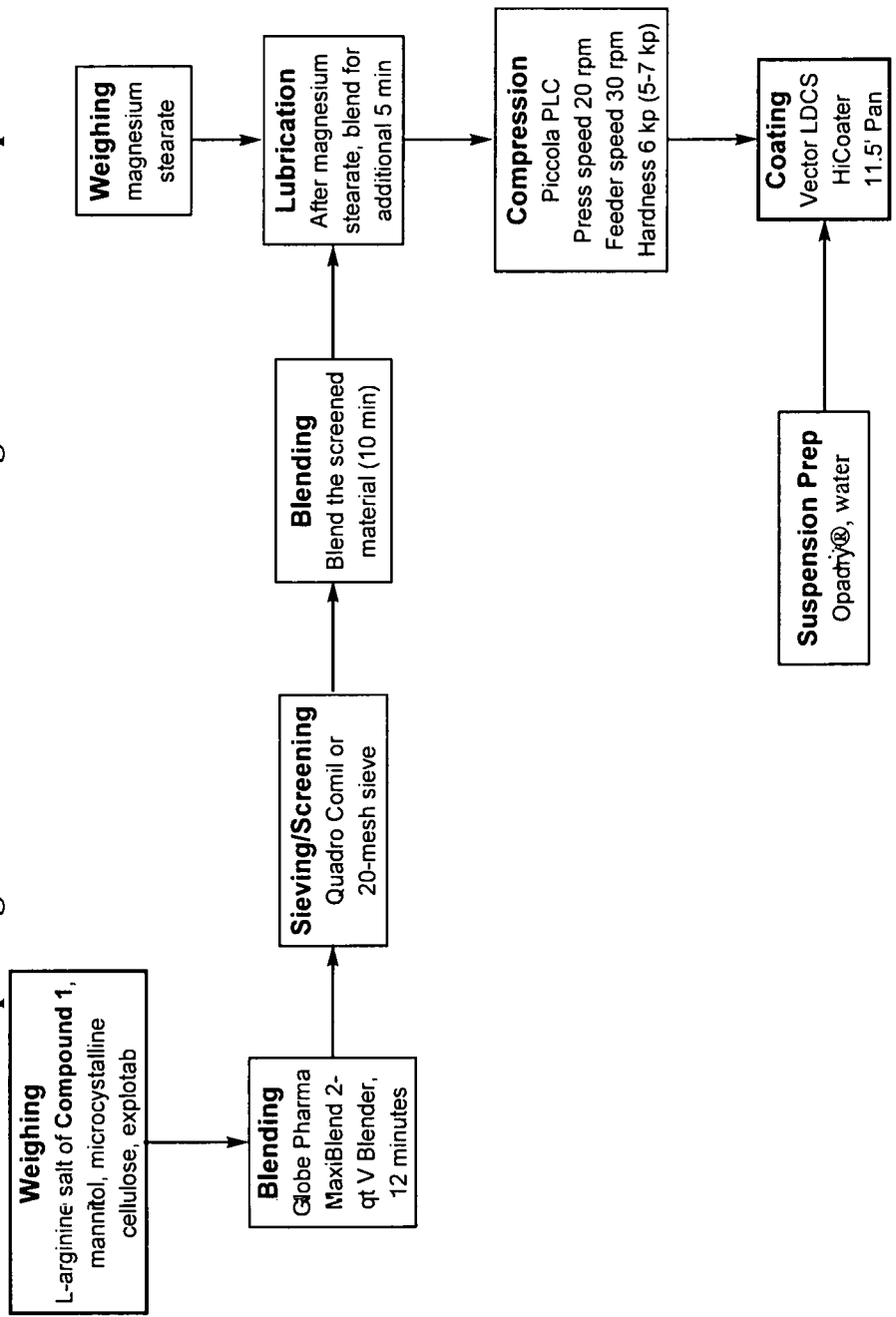
FIG. 4 shows a flowchart for the preparation of core tablets of the L-arginine salt of (R)-2-(7-(4-cyclopentyl-3-(trifluoromethyl)benzyloxy)-1,2,3,4-tetrahydrocyclopenta[b]indol-3-yl)acetic acid (Compound 1).

Example 5: Formulations for L-Arginine Salt of (R)-2-(7-(4-Cyclopentyl-3-(trifluoromethyl)-benzyloxy)-1,2,3,4-tetrahydrocyclopenta[b]indol-3-yl) acetic Acid Core tablets were manufactured using the formulation as described in Table 2 and using substantially the same process as described in FIG. 4. The L-arginine salt of (R)-2-(7-(4-cyclopentyl-3-(trifluoromethyl)benzyloxy)-1,2, 3,4-tetrahydrocyclopenta[b]indol-3-yl)acetic acid is 72.42% free acid (Compound 1) and 27.58% L-arginine (i.e., 1.381 mg of the L-arginine salt of Compound 1 corresponds to 1 mg of active/free acid).

TABLE 2

| Tablet Strength | 1 mg | 2 mg |
|---|---|---|
| L-Arg Salt of Compound 1 | 1.381 | 2.762 |
| Mannitol Pearlitol ® 100SD | 54.119 | 52.738 |
| Microcrystalline cellulose - Avicel ® | 40 | 40 |
| Sodium Starch Glycolate - Explotab ® | 4 | 4 |
| Magnesium Stearate | 0.5 | 0.5 |
| Opadry ® II Blue | 4 | 4 |
| Total tablet target weight | 104 | 104 |

Those skilled in the art will recognize that various modifications, additions, substitutions, and variations to the illustrative examples set forth herein can be made without departing from the spirit of the invention and are, therefore, considered within the scope of the invention.

What is claimed is:

1. A method of treating pyoderma gangrenosum (PG) in an individual in need thereof, comprising administering a therapeutically effective amount of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, wherein the Compound 1, or a pharmaceutically acceptable salt, hydrate, or solvate thereof, is an L-arginine salt of Compound 1.

2. The method according to claim 1, further comprising administering the L-arginine salt of Compound 1 in combination with a therapeutically effective amount of a corticosteroid selected from the group consisting of: dexamethasone, hydrocortisone, methylprednisolone, prednisolone, prednisone, triamcinolone, and fludrocortisone.

3. The method according to claim 1, wherein the PG is an active PG.

4. The method according to claim 1, wherein the individual has at least one condition selected from the group consisting of: an inflammatory bowel disease, arthritis, a hematological disease, and an autoinflammatory disease.

5. The method according to claim 1, wherein the individual has at least one condition selected from the group consisting of: ulcerative colitis and Crohn's disease.

6. The method according to claim 1, further comprising administering the L-arginine salt of Compound 1 in combination with a therapeutically effective amount of a compound selected from the group consisting of: a corticosteroid, an immunosuppressant, a biologic, an anti-inflammatory agent, and an antibiotic.

7. The method according to claim 1, wherein the pyoderma gangrenosum is classic pyoderma gangrenosum.

8. The method according to claim 1, wherein the individual is experiencing an inflammatory episode of pyoderma gangrenosum.

9. The method according to claim 1, wherein the pyoderma gangrenosum is selected from at least one of the following: peristomal pyoderma gangrenosum, bullous pyoderma gangrenosum, pustular pyoderma gangrenosum, and vegetative pyoderma gangrenosum.

10. The method according to claim 1, wherein the individual has at least one active pyoderma gangrenosum ulcer.

11. The method according to claim 1, wherein the individual has at least one active, non-healing pyoderma gangrenosum ulcer.

12. The method according to claim 1, wherein the individual does not have inflammatory bowel disease.

13. The method according to claim 1, wherein the individual does not have ulcerative colitis.

14. The method according to claim 1, wherein the individual does not have Crohn's disease.

15. The method according to claim 1, wherein the L-arginine salt of Compound 1 is in an amount equivalent to about 1 mg to about 5 mg of Compound 1.

16. The method according to claim 1, wherein the L-arginine salt of Compound 1 is an anhydrous, non-solvated crystalline form of the L-arginine salt of Compound 1.

17. The method according to claim 1, wherein the L-arginine salt of Compound 1 is a crystalline free-plate habit of the non-solvated L-arginine salt of Compound 1.

18. The method according to claim 1, wherein the L-arginine salt of Compound 1 is administered orally.

19. The method according to claim 1, wherein the L-arginine salt of Compound 1 is administered once daily.

20. A method of treating pyoderma gangrenosum (PG) in an individual in need thereof comprising administering a therapeutically effective amount of (R)-2-(7-(4-cyclopentyl-3-(trifluoromethyl)benzyloxy)-1,2,3,4-tetrahydrocyclopenta[b]indol-3-yl)acetic acid (Compound 1), or a pharmaceutically acceptable salt, hydrate, or solvate thereof, in an amount equivalent to about 1 mg to about 5 mg of Compound 1.

21. The method according to claim 20, wherein the Compound 1, or a pharmaceutically acceptable salt, hydrate, or solvate thereof, is in an amount equivalent to about 1 mg to about 2 mg.

22. The method according to claim 20, wherein the Compound 1, or a pharmaceutically acceptable salt, hydrate, or solvate thereof, is in an amount equivalent to about 1 mg of Compound 1.

23. The method according to claim 20, wherein the Compound 1, or a pharmaceutically acceptable salt, hydrate, or solvate thereof, is in an amount equivalent to about 2 mg of Compound 1.

* * * * *